United States Patent
Wang et al.

(10) Patent No.: US 6,734,968 B1
(45) Date of Patent: May 11, 2004

(54) SYSTEM FOR ANALYZING SURFACE CHARACTERISTICS WITH SELF-CALIBRATING CAPABILITY

(76) Inventors: Haiming Wang, 40760 Laguna Pl., Fremont, CA (US) 94539; Patrick M. Maxton, 2303 Bentley Ridge Dr., San Jose, CA (US) 95138; Kenneth C. Johnson, 2502 Robertson Rd., Santa Clara, CA (US) 95051; Mehrdad Nikoonahad, 271 Oakhurst Pl., Menlo Park, CA (US) 94025

(*) Notice: Subject to any disclaimer, the term of this patent is extended or adjusted under 35 U.S.C. 154(b) by 0 days.

(21) Appl. No.: 09/298,007

(22) Filed: Apr. 22, 1999

Related U.S. Application Data

(63) Continuation-in-part of application No. 09/246,922, filed on Feb. 9, 1999, now Pat. No. 6,184,984.

(51) Int. Cl.[7] .............................................. G01N 21/21
(52) U.S. Cl. ...................................................... 356/369
(58) Field of Search ................................ 356/369, 364; 250/225

(56) References Cited

U.S. PATENT DOCUMENTS

| | | |
|---|---|---|
| 3,880,524 A | 4/1975 | Dill et al. |
| 3,904,293 A | 9/1975 | Gee |
| 3,985,447 A | 10/1976 | Aspnes |
| 4,053,232 A | 10/1977 | Dill et al. |
| 4,306,809 A | 12/1981 | Azzam |
| 4,668,860 A | 5/1987 | Anthon |
| 4,893,932 A | 1/1990 | Knollenberg |
| 5,018,863 A | 5/1991 | Vareille et al. |
| 5,042,951 A | 8/1991 | Gold et al. |
| 5,166,752 A | 11/1992 | Spanier et al. |
| 5,181,080 A | 1/1993 | Fantom et al. |
| 5,333,052 A | 7/1994 | Finarov |
| 5,416,588 A | 5/1995 | Ducharme et al. |

(List continued on next page.)

FOREIGN PATENT DOCUMENTS

| | | |
|---|---|---|
| WO | WO9839633 | 9/1998 |
| WO | WO9902970 | 1/1999 |

OTHER PUBLICATIONS

International Search Report mailed Oct. 27, 2000.
"Design of a scanning ellipsometer by synchronous rotation of the polarizer and analyzer," Liang–Yao Chen et al., *Applied Optics*, vol. 33, No. 7, Mar. 1, 1994, pp. 1299–1305.

(List continued on next page.)

*Primary Examiner*—Zandra V. Smith
(74) *Attorney, Agent, or Firm*—Parsons Hsue & de Runtz LLP

(57) ABSTRACT

Two phase modulators or polarizing elements are employed to modulate the polarization of an interrogating radiation beam before and after the beam has been modified by a sample to be measured. Radiation so modulated and modified by the sample is detected and up to 25 harmonics may be derived from the detected signal. The up to 25 harmonics may be used to derive ellipsometric and system parameters, such as parameters related to the angles of fixed polarizing elements, circular deattenuation, depolarization of the polarizing elements and retardances of phase modulators. A portion of the radiation may be diverted for detecting sample tilt or a change in sample height. A cylindrical objective may be used for focusing the beam onto the sample to illuminate a circular spot on the sample. The above-described self-calibrating ellipsometer may be combined with another optical measurement instrument such as a polarimeter, a spectroreflectometer or another ellipsometer to improve the accuracy of measurement and/or to provide calibration standards for the optical measurement instrument. The self-calibrating ellipsometer as well as the combined system may be used for measuring sample characteristics such as film thickness and depolarization of radiation caused by the sample.

43 Claims, 12 Drawing Sheets

U.S. PATENT DOCUMENTS

| | | | |
|---|---|---|---|
| 5,486,701 A | | 1/1996 | Norton et al. |
| 5,504,581 A | | 4/1996 | Nagata et al. |
| 5,581,350 A | * | 12/1996 | Chen et al. .................. 356/369 |
| 5,596,406 A | | 1/1997 | Rosencwaig et al. |
| 5,608,526 A | | 3/1997 | Piwonka-Corle et al. |
| 5,687,721 A | * | 11/1997 | Kuhls ......................... 356/364 |
| 5,747,813 A | | 5/1998 | Norton et al. |
| 5,859,424 A | | 1/1999 | Norton et al. |
| 5,872,630 A | | 2/1999 | Johs et al. |
| 5,877,859 A | | 3/1999 | Aspnes et al. |
| 5,900,939 A | | 5/1999 | Aspnes et al. |
| 5,956,148 A | * | 9/1999 | Celii ......................... 356/369 |

OTHER PUBLICATIONS

"A Simple Fourier Photopolarimeter with Rotating Polarizer and Analyzer for Measuring Jones and Mueller Matrices," R.M.A. Azzam, *Optics Communications,* vol. 25, No. 2, May 1978, pp. 137–140.

"The Influence of Cell Window Imperfections on the Calibration and Measured Data of Two Types of Rotating–Analyzer Ellipsometers," A. Straaijer et al., *Surface Science 96,* 1980, pp. 217–231.

"Automatic rotating element ellipsometers: Calibration, operation and real–time applications," R.W. Collins, *Rev. Sci. Instrum.* vol. 61, No. 8, Aug. 1990, pp. 20292062.

"Rotating–compensator/analyzer fixed–analyzer ellipsometer: Analysis and comparison to other automatic ellipsometers," D.E. Aspnes et al., *J. Opt. Soc. Am.,* vol. 66, No. 9, Sep. 1976, pp. 949–954.

Partial International Search Report dated Aug. 21, 2000.

Written Opinion mailed Mar. 13, 2001.

"Analysis of Semiconductor Surfaces With Very Thin Native Oxide Layers By Combined Immersion And Multiple Angle Of Incidence Ellipsometry," I. Ohlidal et al., *Applied Surface Science,* 35 (1988–89) pp. 259–273.

"Determination Of The "Optical" Thickness And Of The Filling Factor Of Discontinuous Au Films From Photometric And Ellipsometric Measurements," E. Elizalde eta l., *Optics Communications,* vol. 60, No. 6, Dec. 15, 1986, pp. 378–382.

"Variable Angle Spectroscopic Ellipsometry,"S.A. Alterovitz et al., *Solid State Technology,* Mar. 1988.

"Application of spectroscopic ellipsometry to complex samples," J. L. Freeouf, *Appl. Phys. Lett.,* 53(24), Dec. 12, 1988, pp. 2426–2428.

"Spectroscopic ellipsometry Studies of SIMOX structures and correlation with cross–section TEM," *Vacuum,* vol. 42, Nos. 5/6, 1991, pp. 359–365.

"Spectroscopic Ellipsometry for the Characterization of Thin Films," F. Ferrieu et al., *J. Electrochem. Soc.,* vol. 137, No. 7, Jul. 1990, pp. 2203–2208.

"Rotating–compensator multichannel ellipsometry for characherization of the evolution of nonuniformities in diamond thin–film growth," J. Lee et al., *Applied Physics Letters,* vol. 72, No. 8, Feb. 23, 1998, pp. 900–902.

"Broadband spectral operation of a rotating–compensator ellipsometer," J. Opsal et al., *Thin Solid Films,* 313–314 (1998), pp. 58–61.

"A Self–Calibrating Modulation Ellipsometer," S. Ducharme et al., *SPIE,* vol. 2839, pp. 373–384.

* cited by examiner

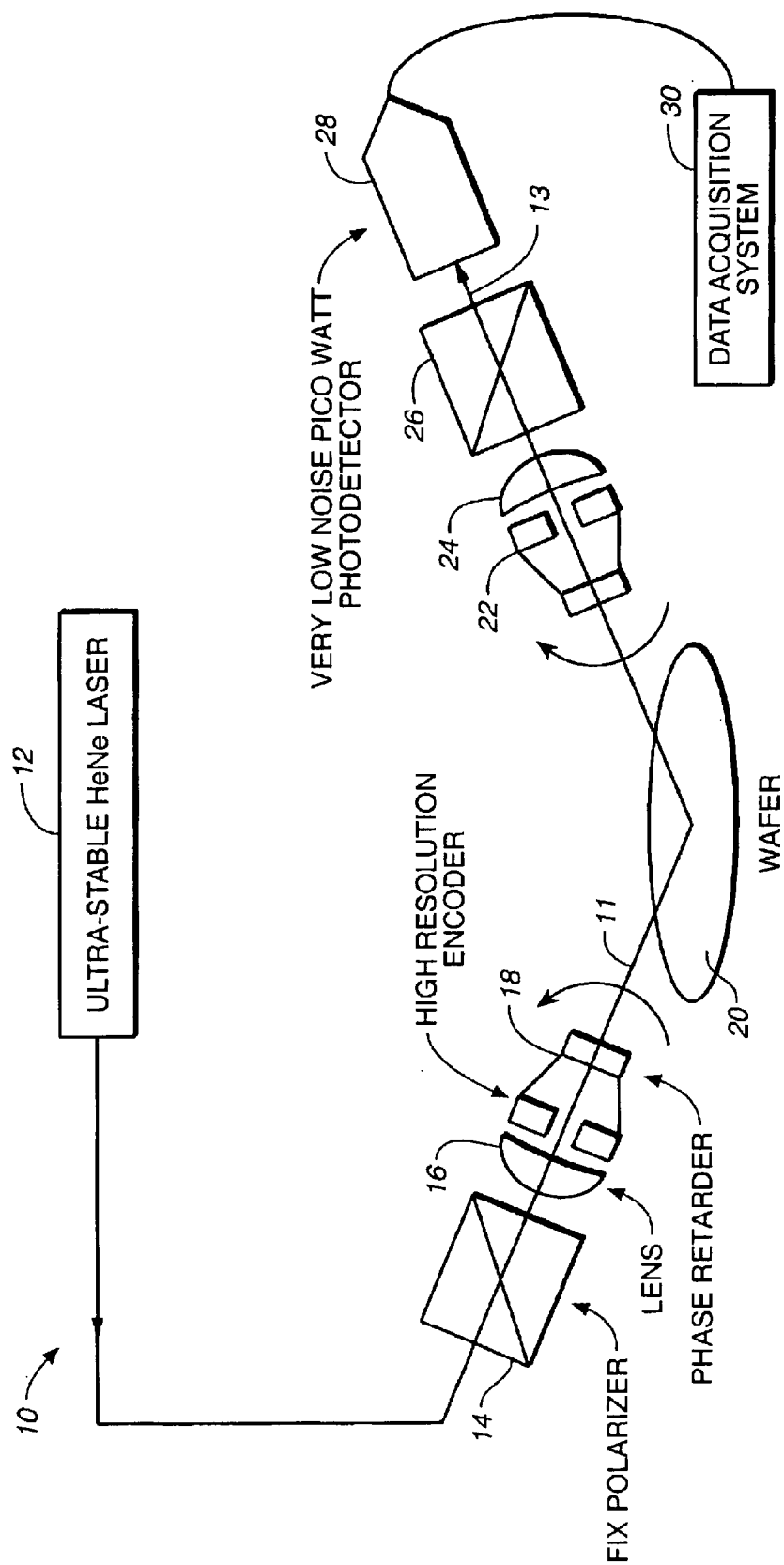
FIG._1

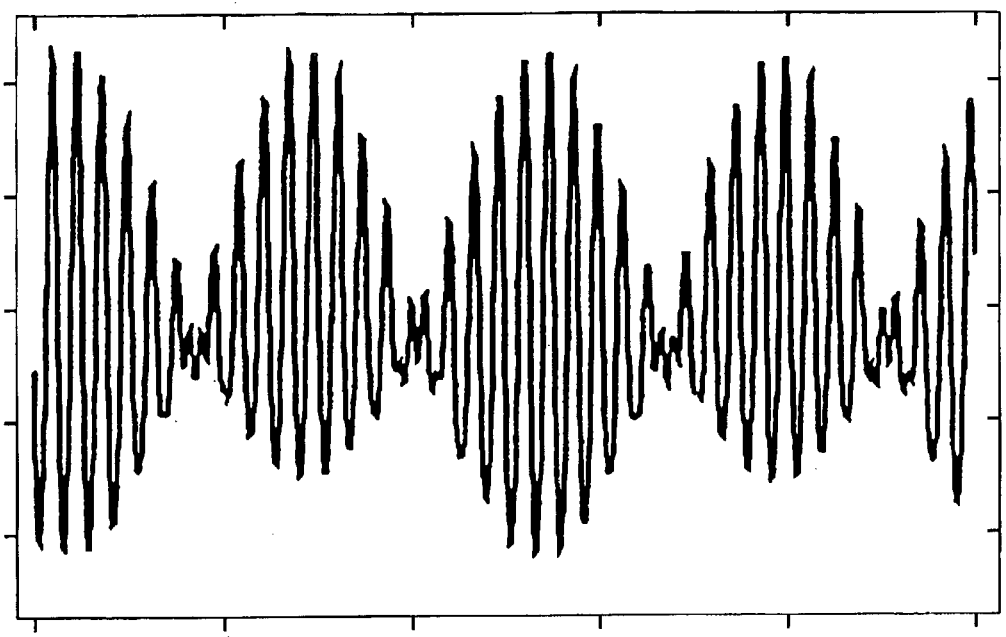
FIG._2
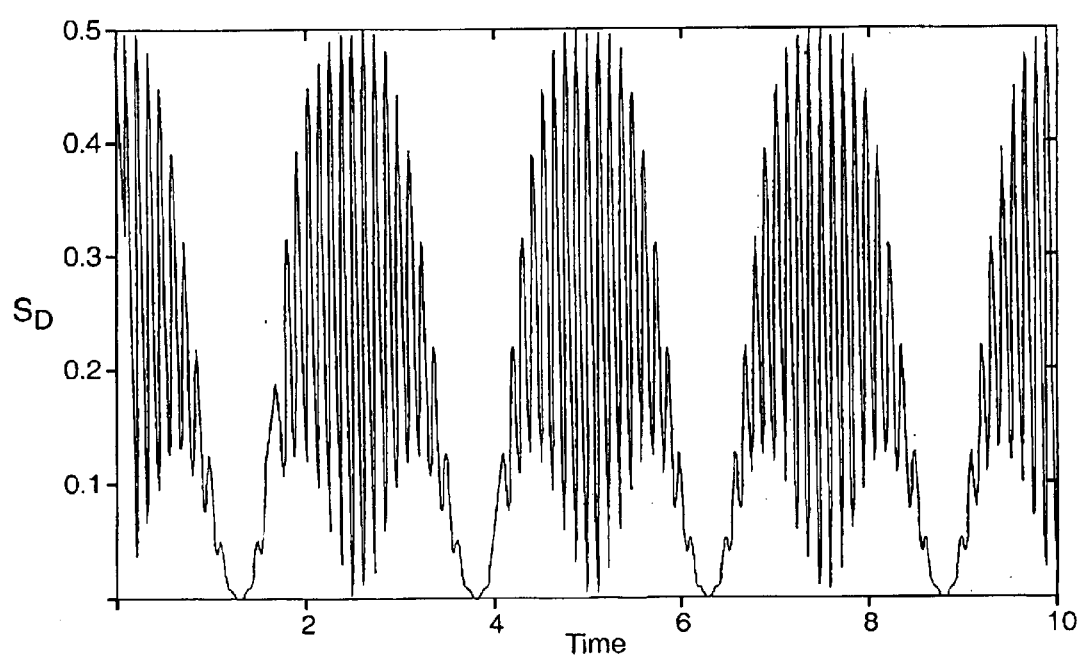
FIG._4

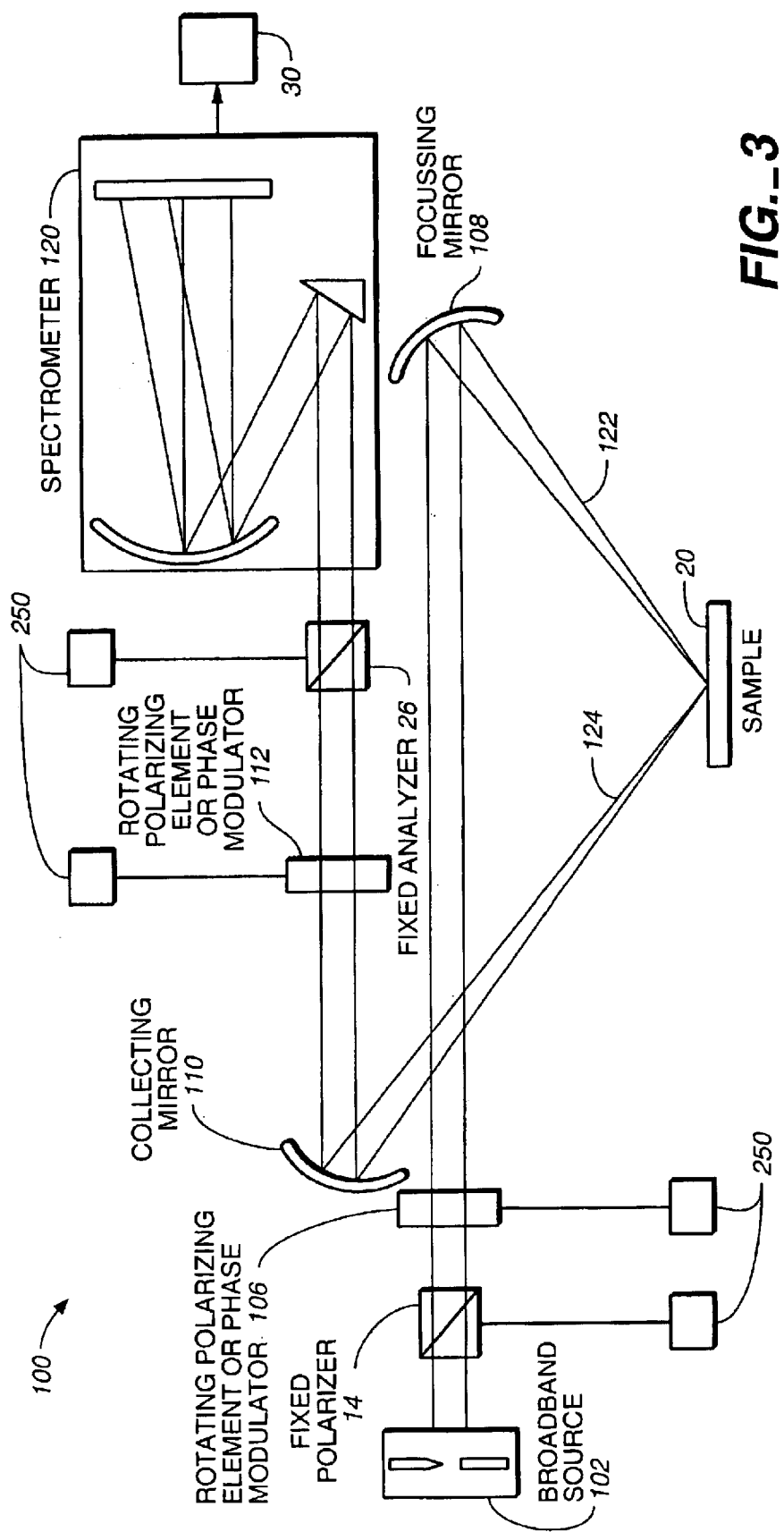
FIG._3

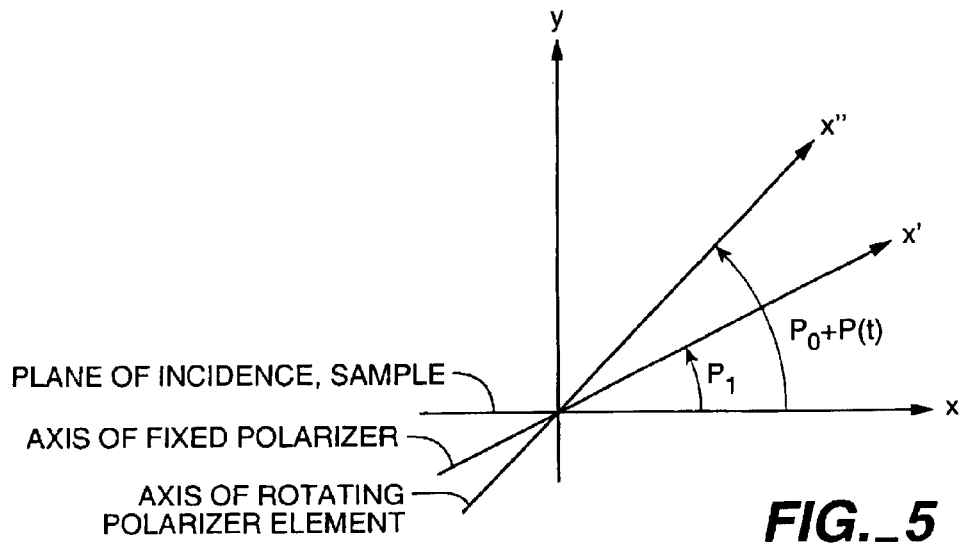
FIG._5
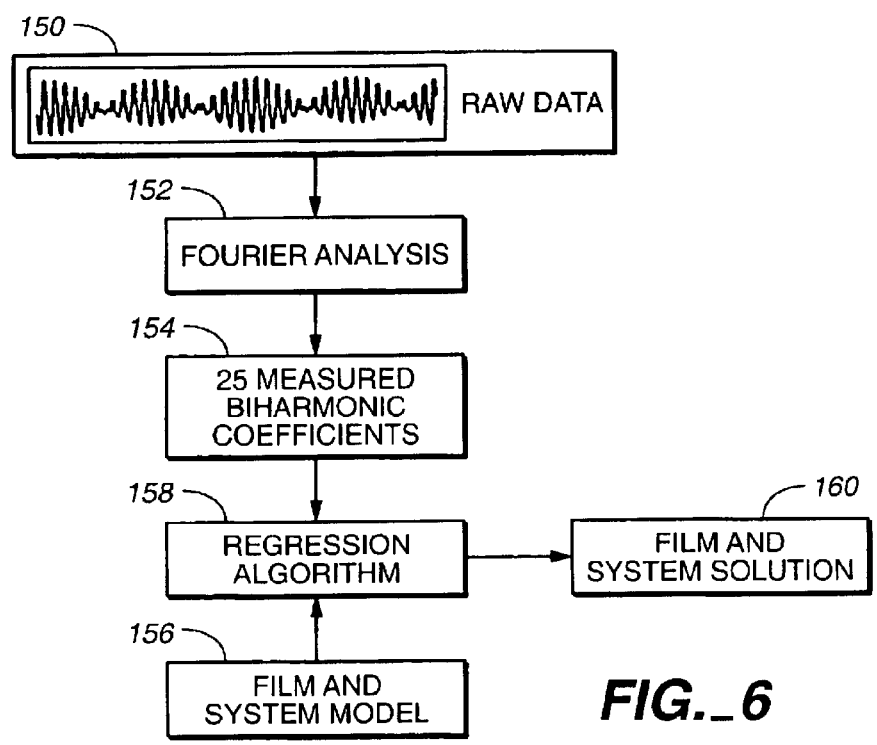
FIG._6

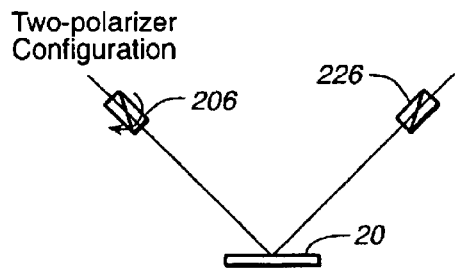

Rotating-polarizer
FIG._7A

Two-polarizer Configuration
206, 226

3 Harmonics.
AOI, $P_1$, $A_0$,
$p_p$, $q_p$, $p_{A0}$, $q_{A0}$,
$S_f(\lambda)$

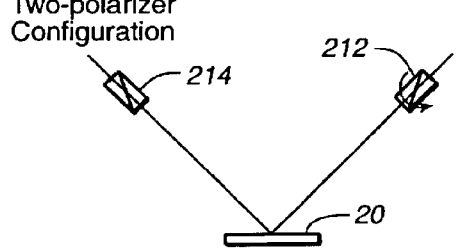

Rotating-analyzer
FIG._7B

Two-polarizer Configuration
214, 212

3 Harmonics.
AOI, $P_0$, $A_1$,
$p_{p0}$, $q_{p0}$, $p_A$, $q_A$,
$S_f(\lambda)$

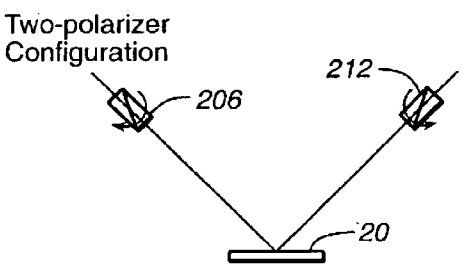

Rotating-both
FIG._7C

Two-polarizer Configuration
206, 212

5 Harmonics,
3 independent.
AOI, $P_1$, $A_1$,
$p_p$, $q_p$, $p_A$, $q_A$,
$S_f(\lambda)$

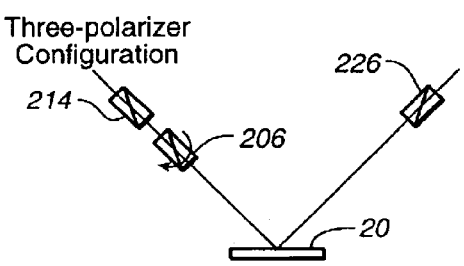

Rotating-polarizer
FIG._7D

Three-polarizer Configuration
214, 206, 226

5 Harmonics.
AOI, $P_0$, $P_1$, $A_0$,
$p_{p0}$, $q_{p0}$, $(p_P, q_P)$, $p_A$, $q_A$,
$S_f(\lambda)$

- $P_0, A_0$ - ANGLES OF FIXED POLARIZER AND ANALYZER
- $P_1, A_1$ - INITIAL ANGLES OF ROTATING POLARIZER AND ANALYZER CORRESPONDING TO ENCODER ZERO
- p, q - UNPOLARIZED AND ELLIPTICALLY POLARIZED FACTORS IN POLARIZER AND ANALYZER MUELLER MATRIX

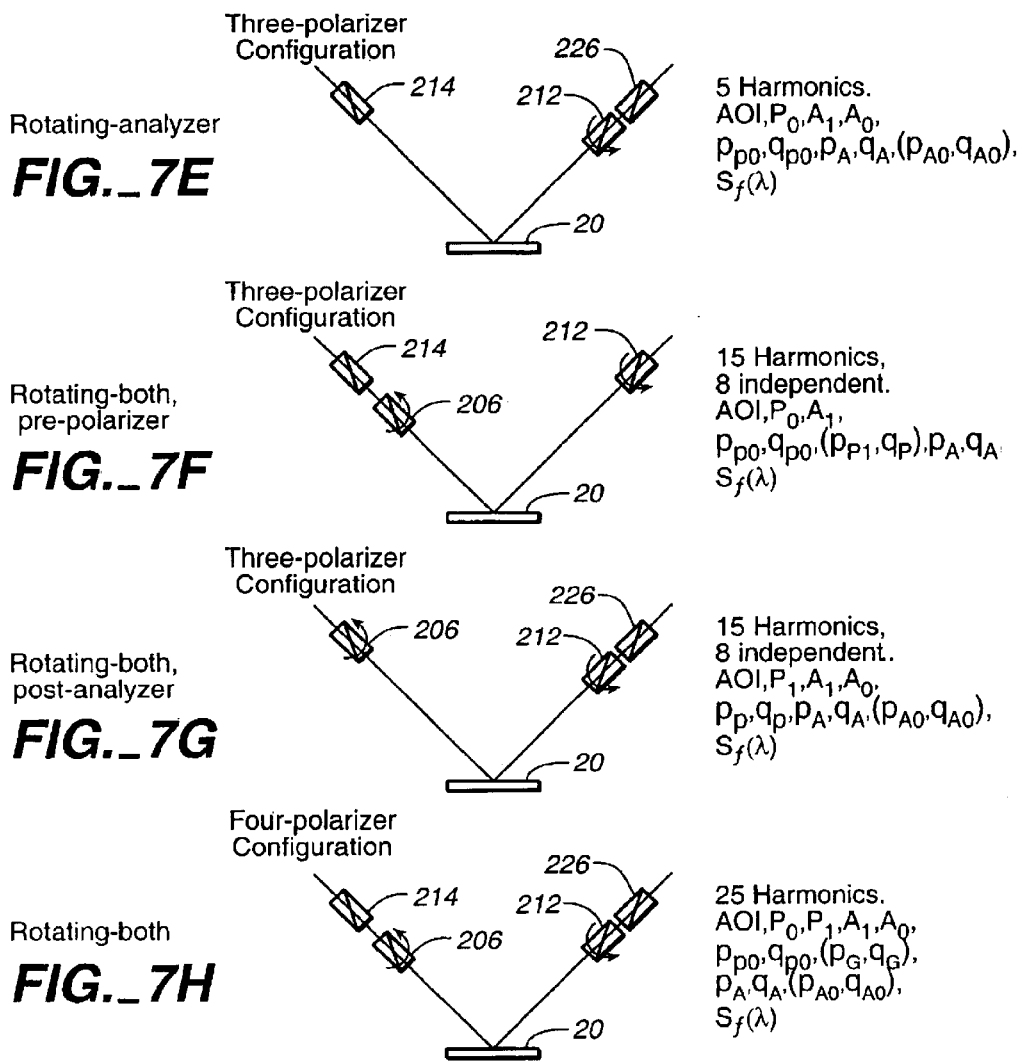

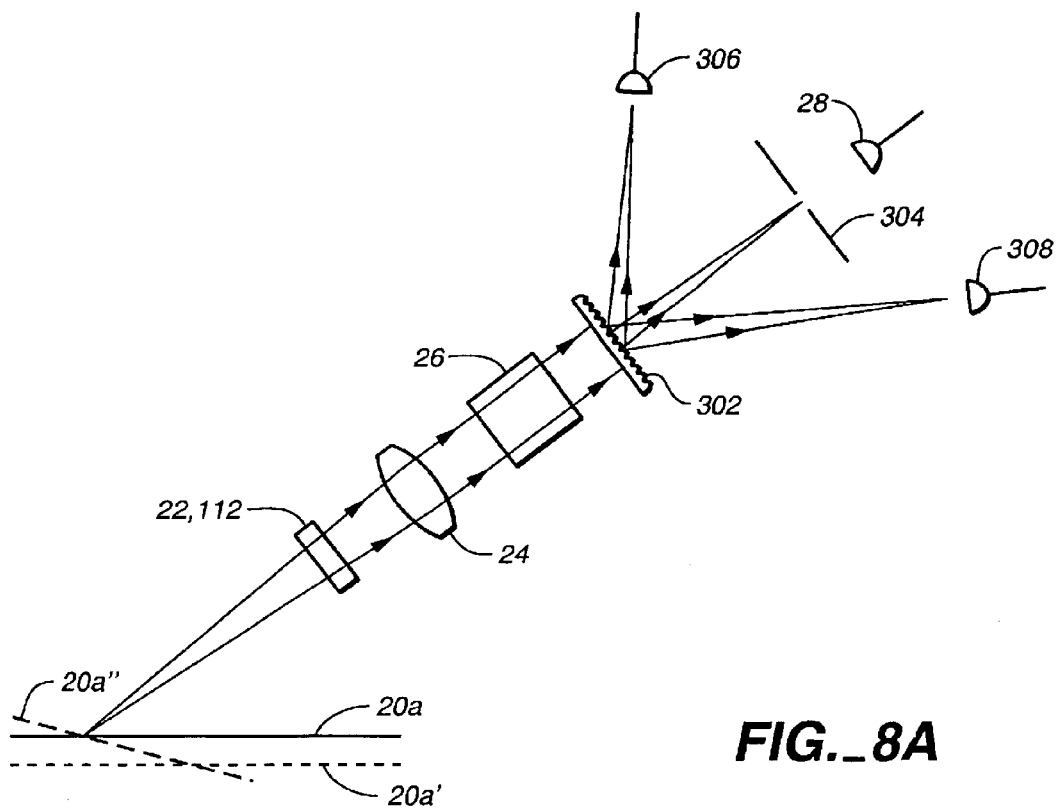
FIG._8A
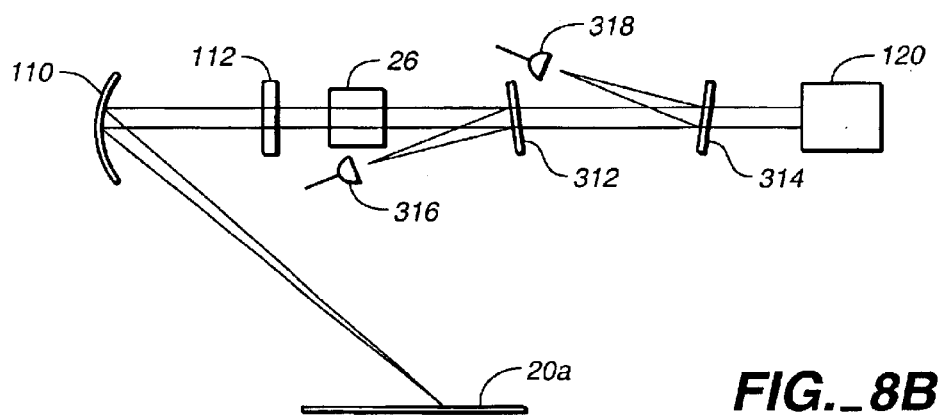
FIG._8B

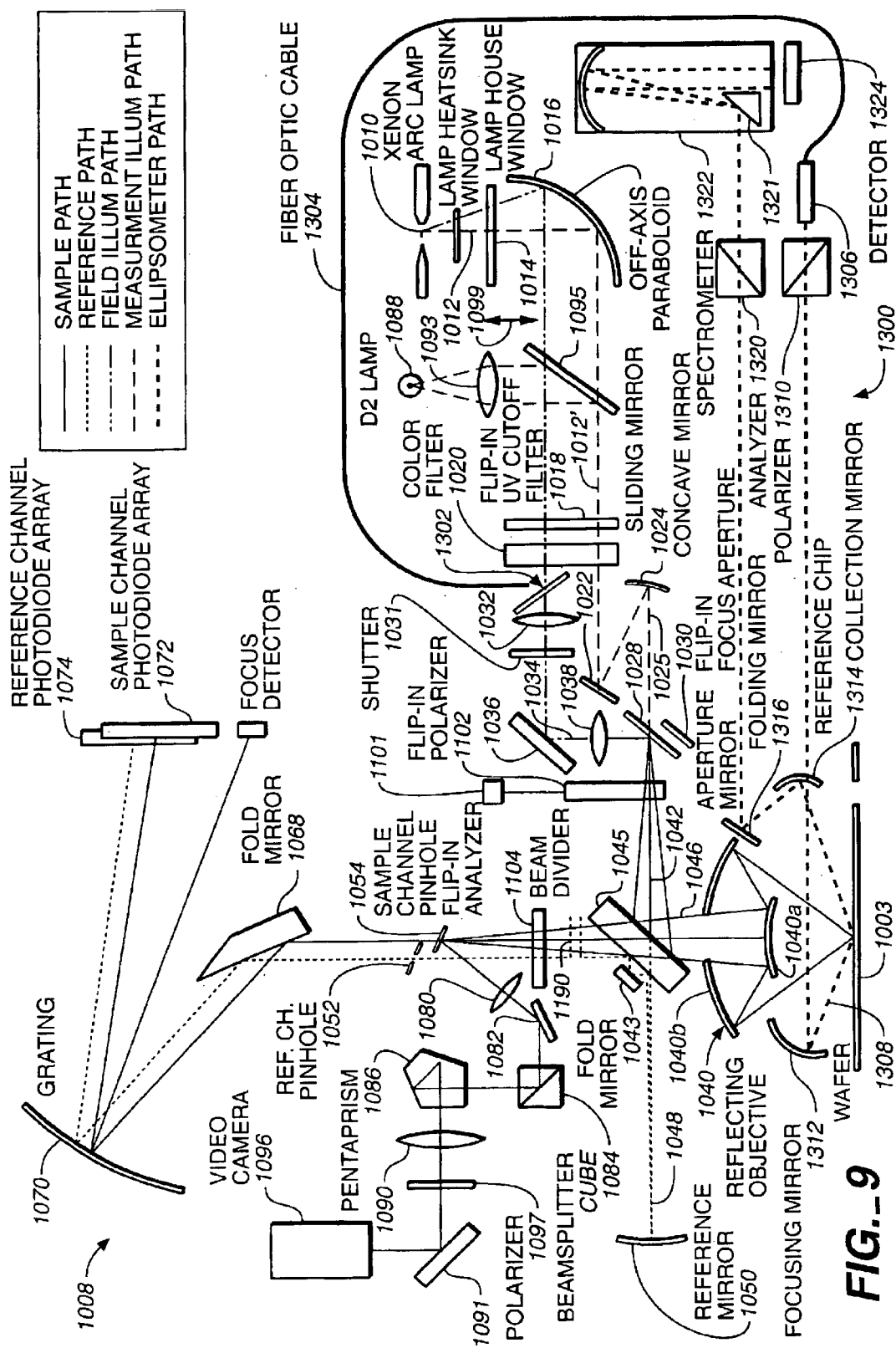
FIG._9

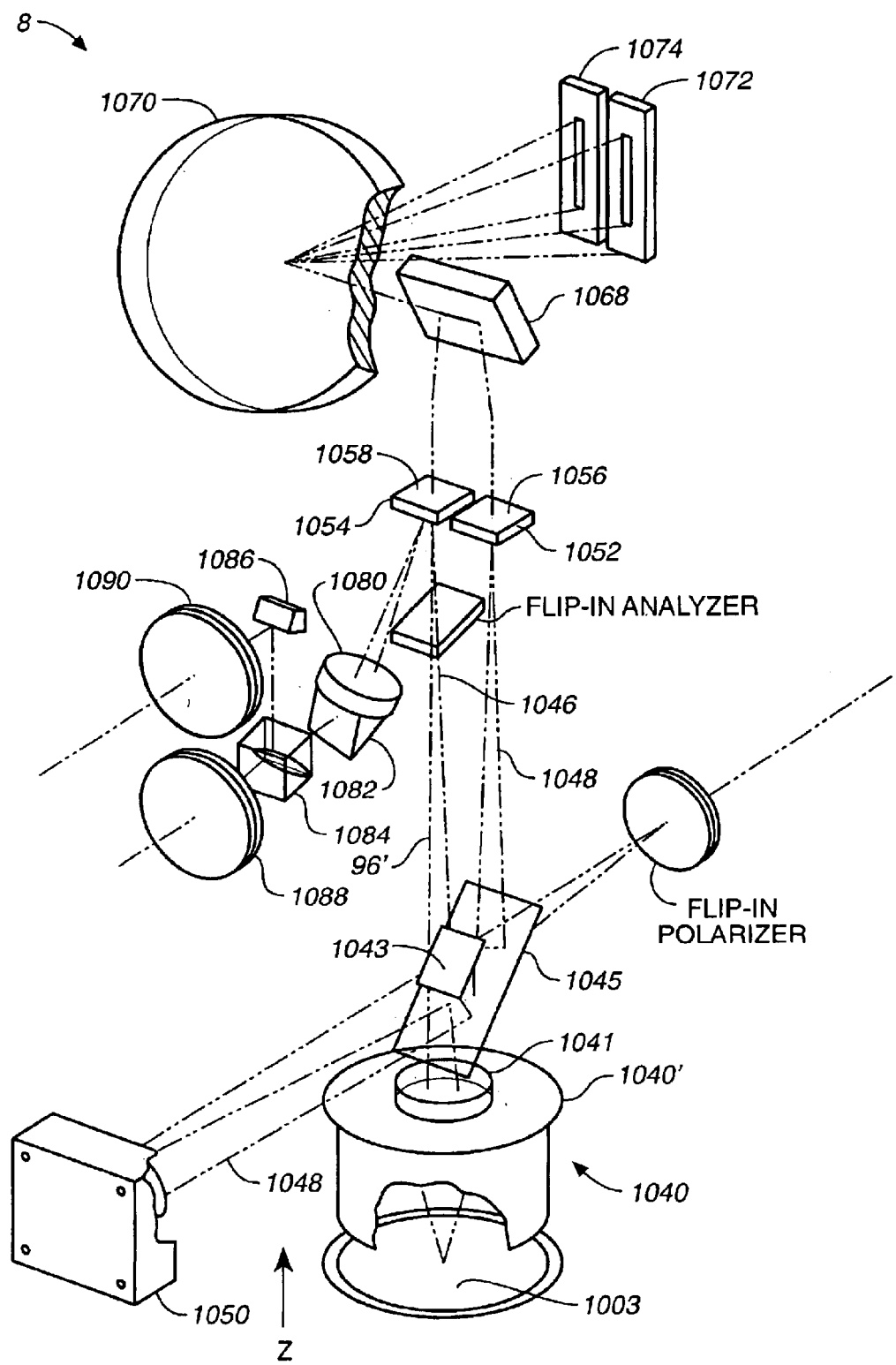
FIG._10

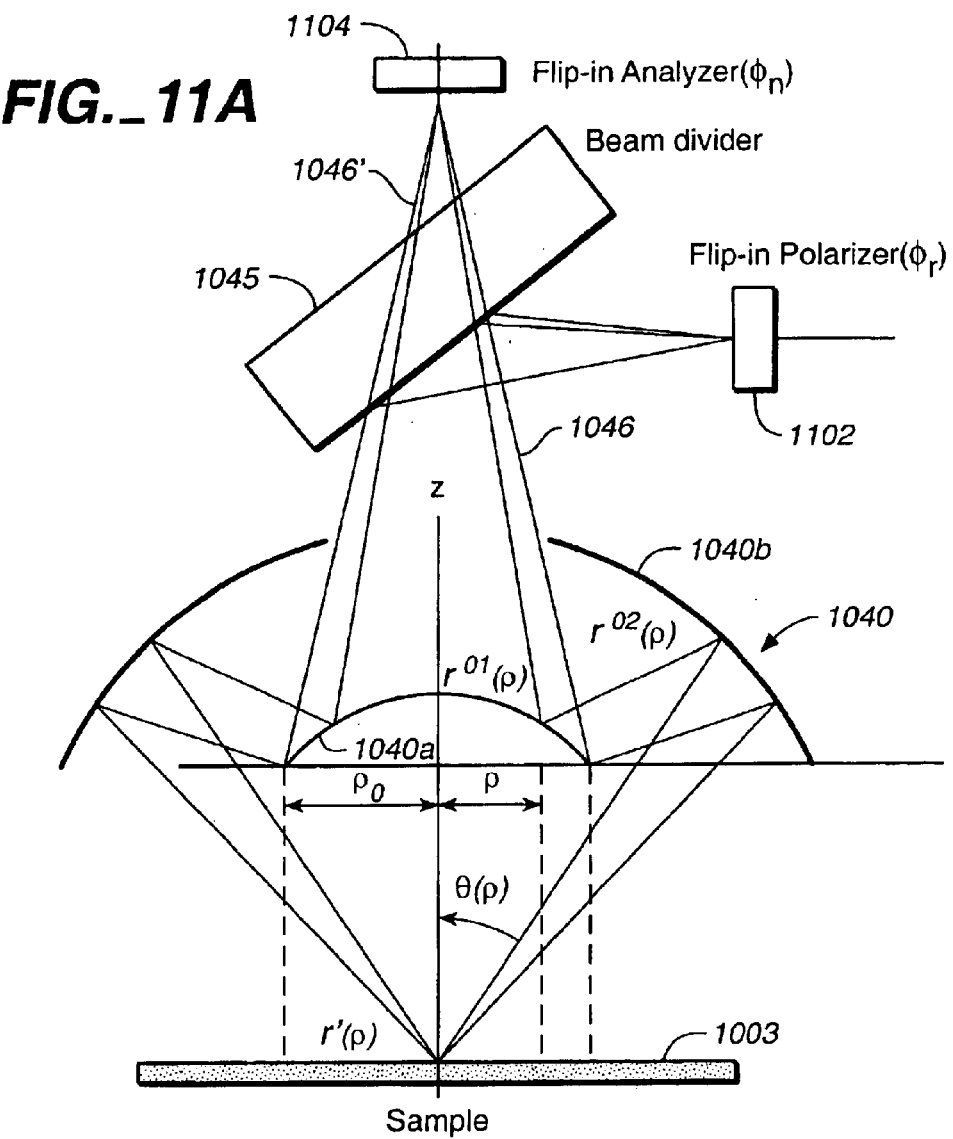
FIG._11A
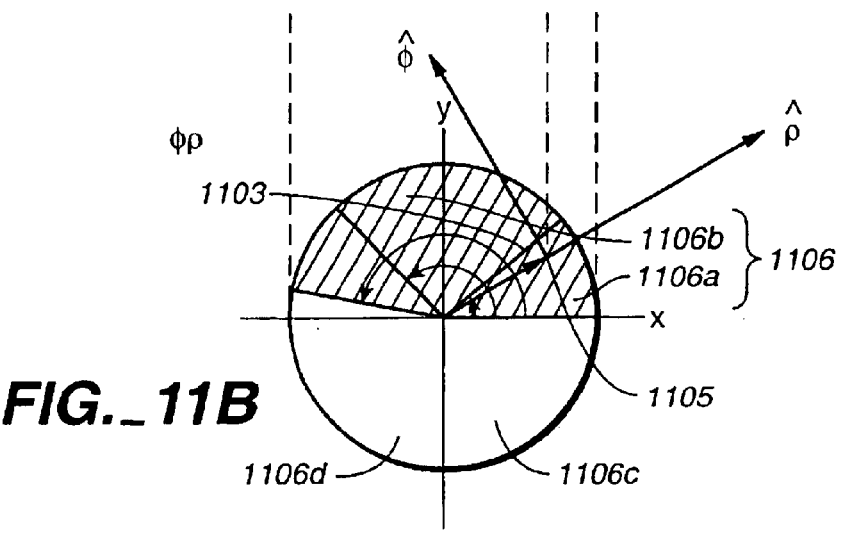
FIG._11B

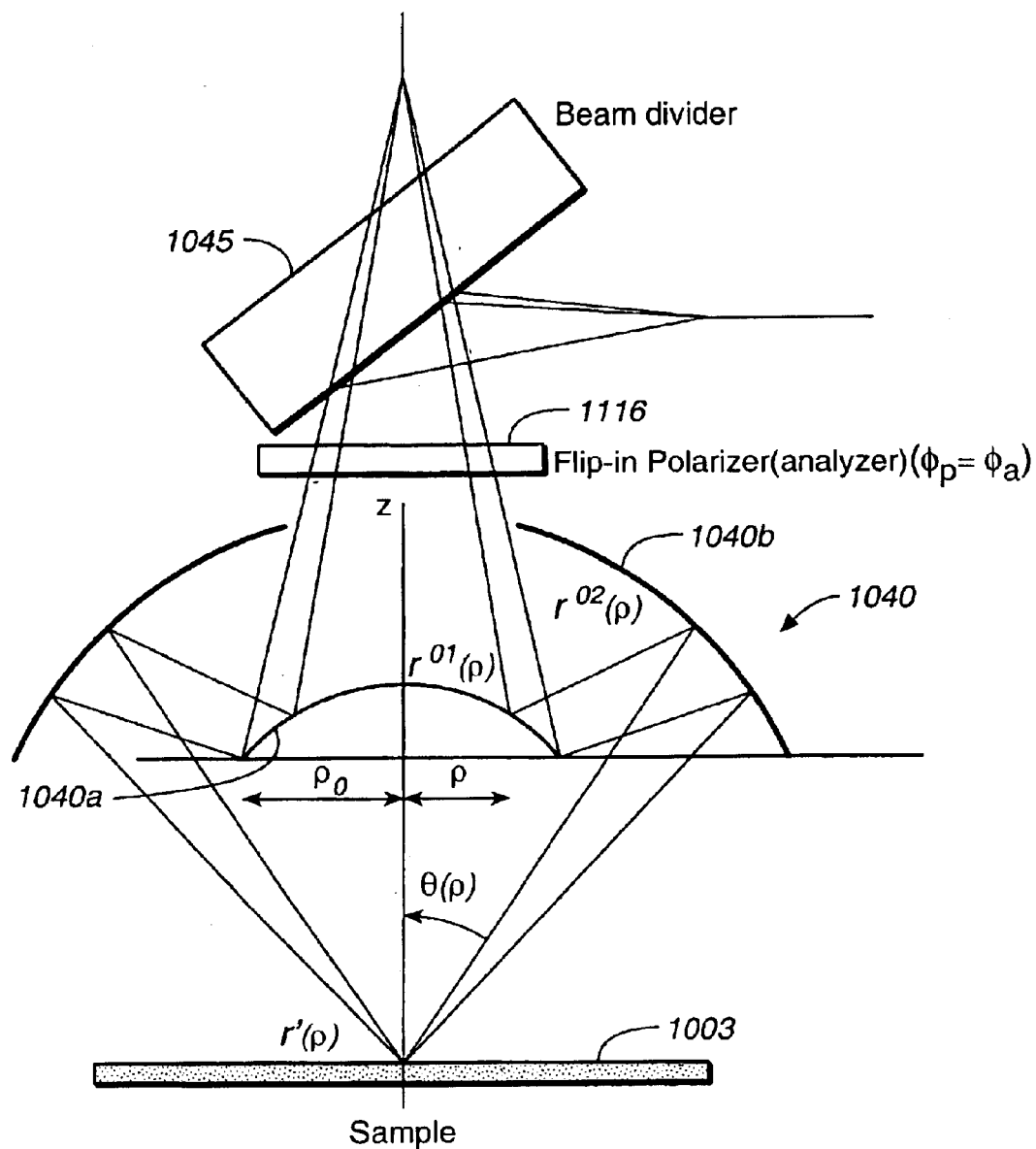
FIG._12

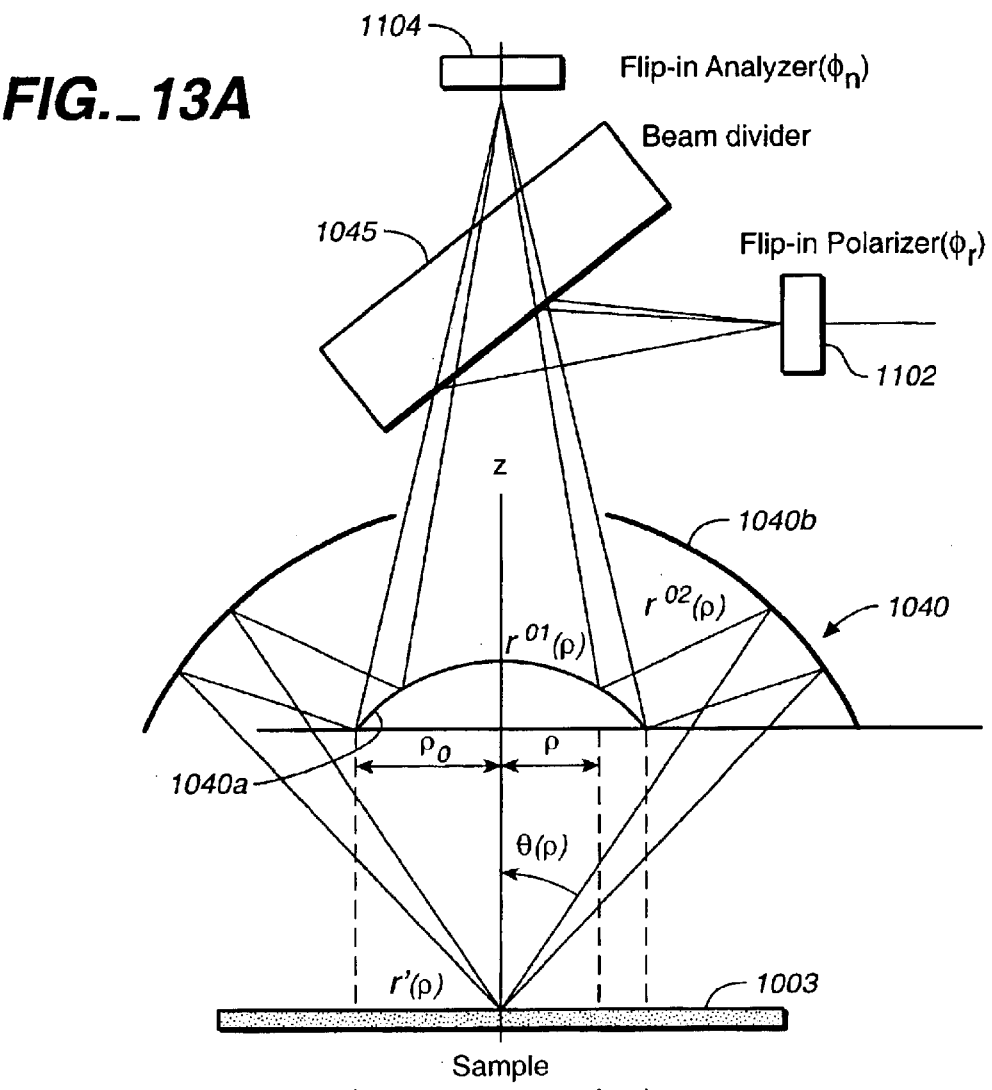
FIG._13A
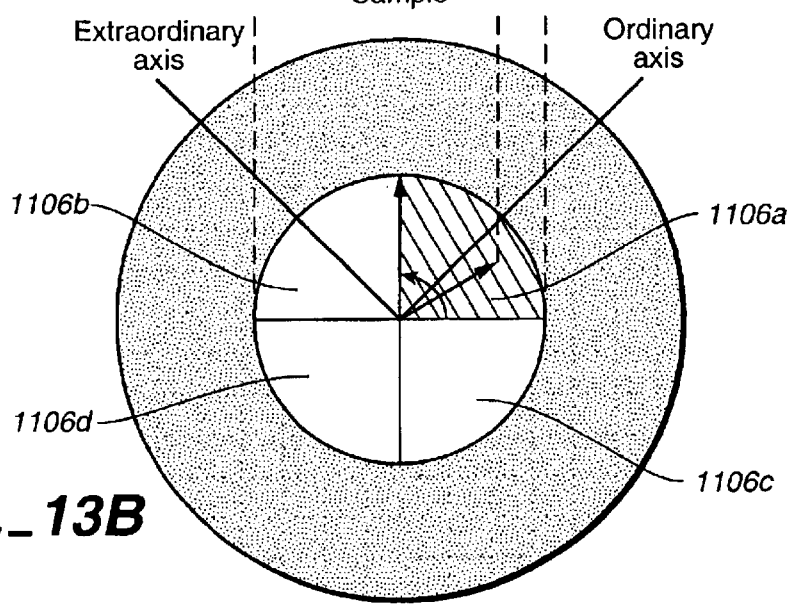
FIG._13B

SYSTEM FOR ANALYZING SURFACE CHARACTERISTICS WITH SELF-CALIBRATING CAPABILITY

CROSS REFERENCE TO RELATED APPLICATION

This is a continuation-in-part of U.S. patent application Ser. No. 09/246,922, now U.S. Pat. No. 6,184,984 filed on Feb. 9, 1999.

BACKGROUND OF THE INVENTION

This invention relates in general to systems for measuring surface characteristics of samples such as semiconductors, and in particular, to such a system with self-calibrating capability.

Spectrophotometers and ellipsometers have been used for measuring surface characteristics such as film thickness and refractive indices of single or multilayer films on substrates such as semiconductors. Materials that are commonly found on semiconductors include oxides, nitrides, polysilicon, titanium and titanium-nitride. Ellipsometers can utilize a single wavelength or broadband light source, a polarizer, a modulator, an analyzer and at least one intensity detector. In this type of conventional ellipsometer, the light from the light source is modulated and sensed by the detector. The detector signal is analyzed to calculate the ellipsometric parameters. This type of ellipsometer is described for example in U.S. Pat. No. 5,608,526.

Ellipsometric measurements are affected by the environment such as temperature changes and mechanical vibrations. For this purpose, ellipsometers are calibrated periodically to account for such environmental effects. Reference samples with known thicknesses and optical characteristics have been used during calibration. However, with the continual downsizing of semiconductor devices, ultra-sensitive ellipsometers have been developed that can measure film layers with thicknesses of the order of angstroms. These systems require reference samples having thin films for accurate calibration. When such thin film reference samples are used, even minimal oxidation or contamination is significant and may result in significant calibration errors. It is therefore desirable to provide an improved surface optical measurement system such as an ellipsometer with better calibration characteristics.

In International Application No. PCT/US98/11562, a stable wavelength calibration ellipsometer is used to precisely determine the thickness of a film on a reference sample. The measured results from the calibration ellipsometer are used to calibrate other optical measurement devices in the thin film optical measurement system. However, this requires the reference sample to be calibrated by means of the calibration ellipsometer each time the thin film optical measurement system is to be used for measurement so that this procedure may be cumbersome. Furthermore, the characteristics of a film or films on the reference sample may have changed between the time of calibration and the time of the measurement, especially where not every measurement is taken immediately after the calibration process.

U.S. Pat. No. 5,416,588 proposes another approach where sufficiently small phase modulation (usually on the order of 3 or 4°) are applied by means of a photo-elastic modulator (PEM). By limiting its phase modulation to several degrees, the detectable signal is proportionally reduced so that the signal-to-noise ratio of the scheme in U.S. Pat. No. 5,416,588 may be less than desirable for a number of applications. By using only small phase modulation, the amount of information obtained concerning the parameters of the measurement system itself will be limited, so that it may be impossible to characterize all of the important system parameters in some systems.

None of the above-described systems are completely satisfactory. It is therefore desirable to provide an ellipsometer with improved calibration characteristics in which the above-described difficulties are not present. It is especially desirable to provide an ellipsometer that has self-calibration capability.

SUMMARY OF THE INVENTION

An ellipsometer with self-calibrating capability is proposed. Instead of having to calibrate the ellipsometer system parameters that may change over time or due to environmental factors, they are derived together with the ellipsometric parameters from the data measured by the ellipsometer. Therefore, there is no need for reference samples or for calibration ellipsometers. All the user needs to do is to derive the system parameters together with the ellipsometric parameters so that any alteration in the system parameters that affect the accuracy of measurement of the ellipsometric parameters may be taken into account. Since the system parameters can be derived from the same data from which the ellipsometric parameters are derived, any change in the system parameters can be accounted for exactly, without having to assume that the system parameters have stayed the same between a calibration process and a measurement process. The invention is also not restricted to small phase modulations. Therefore, the signal-to-noise ratio of the instrument will be adequate for self-calibration in a wide variety of systems and applications.

In the preferred embodiment, a beam of radiation having a linearly polarized component is supplied to the sample. Radiation from the beam that has been modified by the sample is detected. The polarization of the beam of radiation is modulated prior to its detection and one or more ellipsometric parameters of the sample and one or more parameters of a system used in the above process are derived without restrictions as to the magnitude of modulation.

In conventional ellipsometers, essentially unpolarized radiation is provided by the light source to a polarizer to polarize the radiation before it is applied to the sample and radiation from the polarized beam is passed to an analyzer after modification by the sample before the radiation is applied to the detector. In the conventional scheme either the polarizer or the analyzer is rotated but not both. As an improved design in a related aspect of the invention, a beam of radiation is passed through a first rotating polarizer before the beam is applied to the sample. Radiation from the beam after modification by the sample is also modulated by a second rotating polarizer to provide the modulated beam. Radiation from the modulated beam is detected by a detector. From the detector output, one or more ellipsometric parameters of the sample may be obtained. Preferably, system parameters as well as the one or more ellipsometric parameters are derived from the detected radiation to self-calibrate the system and to improve the accuracy of the measurement. Also preferably the beam of radiation is passed through a fixed polarizer between the radiation source and the detector.

As yet another improved design, radiation from a beam having a polarized component is supplied to the sample. Radiation from the beam that has been modulated by the sample is detected. Radiation from the beam is modulated before or after its modification by the sample but before its detection by means of a rotating polarizing element. The modulated radiation that is detected is also passed through a fixed linear polarizer prior to its detection. One or more ellipsometric parameters of the sample may then be derived from the detected radiation.

Another factor that affects the accuracy of measurements in ellipsometers is sample tilt or change of focus due to variations in the heights of the samples. In conventional ellipsometry, the optical paths used for detecting the accuracy of focusing and sample tilt are separate from those used for ellipsometric measurement. This results in errors or instability due to drift or misalignment between the two subsystems. This invention contemplates that a portion of the radiation directed towards the detector is diverted to a position sensitive detector for detecting sample tilt or inaccuracy in focusing due to factors such as changes in sample height. This feature may be used in ellipsometry as well as other surface optical measurement systems such as spectrophotometry.

Semiconductor manufacturing frequently reserves on a wafer a small electrical contact pad which can be used for ellipsometric measurements, where the area frequently have square shapes. The illumination beam in ellipsometry is typically directed at an oblique angle to the sample. Therefore, if the illumination beam has a circular cross-section, the resulting illuminated spot on the sample will be elliptical in shape. Since the size of the square pads reserved for ellipsometry on semiconductors may be small in size, it may be difficult to fit the elliptical spot within such pads. By using a cylindrical objective to focus the illumination beam onto the sample, this would have the effect of flattening the elliptical spot to better fit within the confines of the pads. Preferably, the cylindrical objective focuses the illumination beam to a spot which is substantially circular in shape.

The above described ellipsometer may be advantageously used together with another optical instrument for measuring samples. Preferably, the outputs of the ellipsometer and of the other optical instrument may be used to derive sample information as well as parameters of the ellipsometer to improve accuracy of measurement. In one application, the combined system may be used to measure film thickness information of the sample and depolarization of radiation caused by the sample. The depolarization derived may indicate sample characteristics such as surface roughness.

Alternatively, each of various configurations of the ellipsometer may by itself be used for measuring film thickness information and depolarization caused by the sample, with or without also deriving systems parameters of the ellipsometer from the same measurement output.

BRIEF DESCRIPTION OF THE DRAWINGS

FIG. 1 illustrates an ellipsometer employing two phase retarders to illustrate a first embodiment of the invention.

FIG. 2 is a graphical plot to illustrate an example of detector signals as a function of time at the detector output of the system of FIG. 1.

FIG. 3 illustrates a self-calibration ellipsometer employing two rotating polarizing elements to illustrate a second embodiment of the invention.

FIG. 4 is a graphical plot of the detector signal over time to illustrate an output of the detector of the system of FIG. 3.

FIG. 5 is a schematic view illustrating the angle definitions of various elements modifying the polarization of radiation directed to the sample.

FIG. 6 is a flow chart illustrating a method for deriving an ellipsometric and system parameters in the system of FIGS. 1 and 3 to illustrate the invention.

FIGS. 7A–7H illustrates eight self-calibration ellipsometers each of which employing two or more polarizing elements or a combination of phase retarder(s) and polarizing element(s) to illustrate additional embodiments of the invention.

FIG. 8A is a schematic view of a portion of the systems of FIG. 1 and of a sample tilt and focusing detection subsystem to illustrate another aspect of the invention.

FIG. 8B is a schematic view of a portion of the systems of FIG. 3 and of a sample tilt and focusing detection subsystem to illustrate another aspect of the invention.

FIG. 9 is a schematic view of a combined instrument including a spectroscopic ellipsometer and a polarimetric system to illustrate the preferred embodiment of the invention of the parent application.

FIG. 10 is a perspective view of the polarimetric system of FIG. 9.

FIG. 11A is a simplified schematic view of a portion of the system of FIG. 9 for measuring polarimetric parameters.

FIG. 11B is a graphical illustration of the illuminating aperture of FIG. 11A.

FIG. 12 is a simplified schematic view of a portion of a system for measuring polarimetric parameters to illustrate an alternative embodiment of the invention of the parent application.

FIG. 13A is a simplified schematic view of the system for measuring polarimetric parameters of FIG. 9 where the optical path of the illumination beam or the reflected beam is passed through an aperture to illustrate the preferred embodiment of the invention of the parent application.

FIG. 13B is a schematic view of the aperture of FIG. 13A relative to axes of birefringence of the sample to illustrate the invention of the parent application.

For simplicity in description, identical components in this application are identified by the same numerals.

DETAILED DESCRIPTION OF THE PREFERRED EMBODIMENT

FIG. 1 illustrates an ellipsometer employing two phase retarders to illustrate a first embodiment of the invention. As shown in FIG. 1, ellipsometer 10 includes a source of radiation 12, which may supply radiation of substantially a single wavelength. To supply radiation of substantially a single wavelength, an ultrastable Helium Neon laser may be used. The radiation from source 12 is passed through a fixed polarizer 14. Fixed polarizer 14 is such that it causes the radiation that passes through it to have a linearly polarized component. Fixed polarizer 14 is preferably a linear polarizer fixed in its orientation with respect to the remaining optical components of system 10. Alternatively, fixed polarizer 14 may cause the radiation passing through it to have an elliptical polarization, which includes a linearly polarized component. While preferably radiation having a linearly polarized component is supplied to modulator 16 as described, it will be understood that this is not required and that radiation having a polarized component supplied to modulator 16 is adequate and is within the scope of the invention.

Radiation 11 having a polarized component, preferably a linearly polarized component, emerging from polarizer 14 is focused by lens 16 and passed through a phase retarder 18 and applied to the surface of a sample such as a semiconductor wafer 20 which modifies the polarization of the radiation, such as by reflection, including the polarization state of the polarized component. For samples other than semiconductor wafers, the radiation may be modified by the sample through transmission, scattering, diffraction or still other types of processes; such and other variations are within the scope of the invention. After being modified by sample 20, the modified radiation 13 is passed through a second phase retarder 22 and collected by lens 24 and passed through a second fixed polarizer 26 and applied to a low noise photodetector 28.

Retarders 18 and 22 are rotated at different speeds to modulate the polarization of the radiation before and after modification by the sample 20. The radiation detected by detector 28 is supplied to a data acquisition 30 to derive the ellipsometric parameters of wafer 20.

The system 10 differs from the polarimeter proposed by Azzam in U.S. Pat. No. 4,306,809 which is incorporated herein in its entirety by reference. Azzam derives the Mueller matrix of a sample. System 10 can be used to derive not only the ellipsometric parameters using the detected radiation from detector 28, but also parameters of the components in system 10 itself. These system parameters include, for example, the overall scale factor, the angles (orientation of the polarization axis) and circular deattenuation of the fixed polarizer 14 and analyzer 26, and the angles, phases, linear deattenuation as well as amplitudes of polarization modulation (retardances) of retarders 18 and 24, and any polarization in the radiation supplied by source 12. The overall scale factor may include intensity of the radiation source and detector responsivity. The angles of polarizer 14 and analyzer 26 may be altered by sample tilt in a direction transverse to the plane of incidence of the radiation.

As shown more clearly below, using the system of 10 of FIG. 1, 25 harmonics will be generated which are more than adequate for determining both the ellipsometric parameters and the system parameters. Since the system parameters are derived together with the ellipsometric parameters from the output of detector 28, system 10 is self-calibrating so that there is no need to calibrate the system parameters beforehand. There is, therefore, no need to use reference samples for calibration, or calibration instruments at all. Each time a measurement is made, the system parameters are derived simultaneously with the ellipsometric parameters, so that the ellipsometric parameters are accurately derived without being adversely effected by variations in the system parameters, where these system parameters can be calculated exactly as well. Furthermore, system parameters such as deattenuation, depolarization and aperture integration effects may be difficult to calibrate in conventional systems. In contrast, these factors are automatically taken into account in the system 10 of FIG. 1.

FIG. 2 is a graphical plot illustrating an example of the detector signal at the output of detector 28 as a function of time. Instead of phase retarders or other phase modulators, elements 18, 22 may also be polarizers.

FIG. 3 illustrates a self-calibrating broadband ellipsometer 100 employing two rotating polarizing elements or phase retarders to illustrate the second embodiment of the invention. First, it is assumed that two rotating polarizer elements are used in system 100. As shown in FIG. 3, system 100 includes a broadband source 102. To supply broadband radiation, it may be desirable to use a xenon lamp as well as a deuterium lamp to cover a broad spectrum that includes the deep ultraviolet region, so that the radiation supplied by source 12 may range from 190 to about 1 micron. Obviously, light sources that supply multiple wavelength radiation (e.g. from several lasers) or other wavelengths may also be used and are within the scope of the invention.

Fixed polarizer 14 causes the radiation that passes through it to have a polarized component, preferably a linearly polarized component. Radiation having such a component is supplied to a rotating polarizing element or phase modulator 106 and focused by a mirror 108 to sample 20. The radiation that is modified by sample 20, such as by reflection or transmission (or any one of the processes enumerated above for FIG. 1), is collected by a collecting mirror 110 and relayed through rotating polarizing elements 112 to a fixed analyzer 26. The radiation emerging from analyzer 26 is then supplied to a spectrometer 120 for separating the broadband radiation into different wavelength components so that the intensities of the different wavelengths may be detected individually. Such intensities are then supplied to a data acquisition system 30 for analysis.

To avoid chromatic aberration, focusing and collecting mirrors are used in lieu of lenses and a spectrometer is used to separate the different wavelengths in the detected broadband radiation into its wavelength components for detection. Radiation source 102 is a broadband source instead of a laser. FIG. 4 is a graphical plot of the intensity signal at one of the wavelength components detected by spectrometer 20. Different from a system where phase retarders are used, a rotating linear polarizer will permit substantially no radiation to pass when its axis of polarization is perpendicular to that of the fixed polarizer 14. For this reason, the intensity will become substantially 0 periodically.

FIG. 5 is a schematic view illustrating the relative orientations of the plane of incidence, the axis of fixed polarizer 14 and the axis of the rotating polarizing element 106 to illustrate the embodiment of FIG. 3. FIG. 5 is a view along a direction opposite to (i.e. looking into) the direction of the illumination beam 122. As shown in FIG. 5, the reference x axis is along the plane of incidence of the beam 122 directed towards sample 20 and of its reflection 124. The axis of fixed polarizer 14 is along the arrow x' at angle $P_1$ and the axis of the rotating polarizing element 106 is along arrow x" at an angle $P_0+P(t)$ from the x axis. Since element 106 is rotating, its axis changes as a function of time t. Therefore, if $P_0$ is the angle of its axis at time 0, then the angle of its axis at time t is $P_0+P(t)$. A similar quantity $A_0+A(t)$ may be defined for the angle of rotating analyzer 112 with respect to the plane of incidence when viewed along a direction opposite to the direction of modified (reflected, in the case of FIG. 3) beam 124 in FIG. 3. Thus, if polarizing element 106 is rotating at a frequency $f_P$ and the polarizing element 112 is rotating at a frequency $f_A$, the polarization angles of the axes of rotating polarizing elements 106 and 112 are $P_R(t)$, $A_R(t)$ given by Equation 1 below, where t represents time.

$$P_R(t)=P_0+P(t), P(t)=2\pi f_P t$$
$$A_R(t)=A_0+A(t), A(t)=2\pi f_A t \tag{1}$$

where the initial angles $P_0$ and $A_0$ correspond to the initial angles of the polarizer and analyzer elements 106, 112 when t is 0.

The detector signal $S_D^{(m)}$ at spectrometer 120 is then modulated by these rotating polarizing elements, and is recorded as a function of time t where "m" in the expression for the detector signal indicates that this is the measured detector signal rather than a theoretical one from a model. This same notation is used below for other quantities as well.

An example of the detector signal is shown in FIG. 4. As will be shown below, 25 harmonics may be derived from the measured detector signal where the 25 harmonics may be compared with those of a model for deriving the ellipsometric and system parameters. But before such comparison is discussed, it is necessary to first examine a model of the system as explained below.

SYSTEM MODELING

Mueller Matrix Representation of Detector Signal

Analytically, the detector signal can be expressed as:

$$S_D = S'_A(A) M_S S_P(P) \quad (2)$$

where $S_P(P)$: 4×1 Stokes vector of the beam incident on the sample, $M_S$: 4×4 Mueller matrix of the sample, $S'_A(A)$: 1×4 Projection of the first row of the Mueller matrix that represents the elements in the analyzer.

In the last part of Equation 2, for simplicity, P(t) and A(t) are simply written as P, A; it being understood that these are functions of time. The same simplification is made in the description below.

Modeling of Elements in the Polarization Generation Side

The generation side of the system 100 comprises the fixed polarizer 14, rotating polarizer 106 and mirror 108. All system parameters in the generation side and the rotation angle P are encoded in the Stokes vector $S_P(P)$. Mueller formulation is then used to describe the behavior of light in each element on the generation side, and the propagation from one element to another. Assuming the light source 102 is totally unpolarized, the following equation is obtained:

$$S_P(P) = R(P_O + P) M_P R(-P_O - P) R(P_1) M_{PI} R(-P_1) \begin{bmatrix} 1 \\ 0 \\ 0 \\ 0 \end{bmatrix} \quad (3)$$

where

R: Mueller rotation matrix, $M_{P1}$: Mueller matrix of the fixed polarizer 14, $M_P$: Mueller matrix of the rotating polarizing element 106 in the generation side.

Modeling of Elements in the Analyzing Side

The analyzing side comprises mirror 110, rotating polarizer 112, and fixed polarizer 26. All system parameters in the analyzing side and the rotation angle A of polarizer 112 relative to the x axis are encoded in the projection of the first row of the Mueller matrix representing the elements of the analyzing side $S'_A(A)$. Similarly, $$S'_A(A) = [1\ 0\ 0\ 0] R(A_1) M_{A1} R(A_0 + A) M_A R(-A_0 - A) \quad (4)$$

where $M_{A1}$: Mueller matrix of the fixed analyzer 26, $M_A$: Mueller matrix of the rotating polarizing element 112 in the analyzing side.

Fourier Analysis

Harmonics related to the rotation angle in the polarization generation side Mathematical manipulating Equation (3), it is found that each element in the Stokes vector $S_P(P)$ consists of 5 harmonics: DC, double, and quadruple-harmonics of the rotation frequency $f_P$:

$$S_P(P) = \begin{bmatrix} S_{P0}(P) \\ S_{P1}(P) \\ S_{P2}(P) \\ S_{P3}(P) \end{bmatrix} \quad (5)$$

$S_{P0}(P) = a_{00} + a_{01}\cos 2P + a_{02}\sin 2P + a_{03}\cos 4P + a_{04}\sin 4P$
$S_{P1}(P) = a_{10} + a_{11}\cos 2P + a_{12}\sin 2P + a_{13}\cos 4P + a_{14}\sin 4P$
$S_{P2}(P) = a_{20} + a_{21}\cos 2P + a_{22}\sin 2P + a_{23}\cos 4P + a_{24}\sin 4P$
$S_{P3}(P) = a_{30} + a_{31}\cos 2P + a_{32}\sin 2P + a_{33}\cos 4P + a_{34}\sin 4P$ where $a_{00}$, $a_{01}$, are the coefficients that characterize the generation side of system 100.

Harmonics Related to the Rotation Angle in the Analyzing Side

Similarly, the first row of the analyzing side Mueller matrix also consists of 5 harmonics:

$$S_A(A) = \begin{bmatrix} S_{A0}(A) \\ S_{A1}(A) \\ S_{A2}(A) \\ S_{A3}(A) \end{bmatrix} \quad (6)$$

$S_{A0}(A) = b_{00} + b_{01}\cos 2A + b_{02}\sin 2A + b_{03}\cos 4A + b_{04}\sin 4A$
$S_{A1}(A) = b_{10} + b_{11}\cos 2A + b_{12}\sin 2A + b_{13}\cos 4A + b_{14}\sin 4A$
$S_{A2}(A) = b_{20} + b_{21}\cos 2A + b_{22}\sin 2A + b_{23}\cos 4A + b_{24}\sin 4A$
$S_{A3}(A) = b_{30} + b_{31}\cos 2A + b_{32}\sin 2A + b_{33}\cos 4A + b_{34}\sin 4A$ where $b_{00}$, $b_{01}$, are the coefficients that characterize the analyzing side of system 100.

Harmonics of the Detector Signal

Obviously, the detector signal consists of 25 harmonics:

$$\begin{aligned} S_D = &\ F_{c0} + F_{c1}\cos 2(P-A) + F_{s1}\sin 2(P-A) + \\ &\ F_{c2}\cos 4(P-A) + F_{s2}\sin 4(P-A) + F_{c3}\cos 2P + \\ &\ F_{s3}\sin 2P + F_{c4}\cos 2A + F_{s4}\sin 2A + F_{c5}\cos(4P-2A) + \\ &\ F_{s5}\sin(4P-2A) + F_{c6}\cos(2P-4A) + F_{s6}\sin(2P-4A) + \\ &\ F_{c7}\cos 4P + F_{s7}\sin 4P + F_{c8}\cos 4A + F_{s8}\sin 4A + \\ &\ F_{c9}\cos 2(P+A) + F_{s9}\sin 2(P+A) + F_{c10}\cos(4P+2A) + \\ &\ F_{s10}\sin(4P+2A) + F_{c11}\cos(2P+4A) + \\ &\ F_{s11}\sin(2P+4A) + F_{c12}\cos 4(P+A) + F_{s12}\sin 4(P+A) \end{aligned} \quad (7)$$

Regression

Regression of Harmonic Coefficients F:

Preferably, 100 to several thousand data points in time domain may be obtained by measurement. Sample structure (film indices and thicknesses) and system parameters (angle of incidence, angles $P_0$, $P_1$, $A_0$, $A_1$, depolarization of the fixed polarizer and analyzer, etc.) may be directly regressed from the detector signal data. However, this regression is nonlinear. Nonlinear regression of thousand data points is not very efficient. On the other hand, regression of F-coefficients is linear, thus improves the efficiency of regression. The minimization of the expression $$\left\| F_{c0}^{(m)} + \sum_{n=1}^{12} F_{cn}^{(m)} x_n + \sum_{n=1}^{12} F_{sn}^{(m)} x_{12+n} - S_D^{(m)} \right\|^2 \quad (8)$$

determines harmonic coefficients $F_{c0}^{(m)}$, $F_{cn}^{(m)}$, and $F_{sn}^{(m)}$, n=1, 2, ... 12. In the regression the vector x is defined as $$x_1 = \cos 2(P-A), x_2 = \cos 4(P-A), \ldots, x_{12} = \cos 4(P+A), x_{13} = \sin 2(P-A), x_{14} = \sin 4(P-A), \ldots, x_{24} = \sin 4(P+A) \quad (9)$$

Regression of the Sample Structure and System Parameters:

In the above linear regression, sample structure and system parameters are not used. On the other hand, the harmonic coefficients are related to the sample structure and system parameters. In fact, they are nonlinear functions related to the sample structure and system parameters. These non-linear relations can be obtained by a system model and film model:

$$F_{c0} = f_{c0}(n, k, d, \lambda, P_0, P_1, A_0, A_1, \ldots)$$
$$F_{c1} = f_{c1}(n, k, d, \lambda, P_0, P_1, A_0, A_1, \ldots)$$
$$\vdots$$
$$F_{c12} = f_{c12}(n, k, d, \lambda, P_0, P_1, A_0, A_1, \ldots) \quad (10)$$
$$F_{s1} = f_{s1}(n, k, d, \lambda, P_0, P_1, A_0, A_1, \ldots)$$
$$\vdots$$
$$F_{s12} = f_{s12}(n, k, d, \lambda, P_0, P_1, A_0, A_1, \ldots)$$

Methods for constructing such system and film model are known to those in the art and will not be elaborated here. This allows us to regress the sample structure and system parameters in the expression (11) below:

$$\|F_{c0} - F_{c0}^{(m)}\|^2 + \sum_{n=1}^{12} \|F_{cn} - F_{cn}^{(m)}\|^2 + \sum_{n=1}^{12} \|F^{sn} - F^{sn(m)}\|^2 \quad (11)$$

where the quantities marked by "m" are those obtained from the measured detector signal from spectrometer 120 as explained above, and those that are not are those from the model.

The process for deriving the ellipsometric and system parameters will now be described in reference to FIG. 6. First, raw data is obtained as described above, which appears at the output of the spectrometer 120 (block 150). Fourier analysis is performed on the data and 25 measured biharmonic coefficients are obtained (blocks 152, 154). A film and system model is constructed as indicated in Equation 10 (block 156). The system parameters that are taken into account may include one, some or all of those discussed above (block 156). The regression algorithm of expression 11 above is then performed (block 158) to solve for the harmonic coefficients F. From these F coefficients, the ellipsometric parameters n, k and the system parameters may then be derived (block 160). The system parameters that may be derived from the spectrometer output include, for example, the overall scale factor, the angles (orientation of the polarization axis) and circular deattenuation of the fixed polarizers 14 and analyzer 26, and the angles, depolarization of polarizer 106 and analyzer 112, and any polarization in the radiation supplied by source 102. The same model and process as those described above can be used where source 102, 12 are replaced by radiation sources with some unpolarized components.

In reference to FIG. 3, where the rotating elements 106, 112 are phase modulators such as phase retarders instead of polarizing elements, equations that are substantially the same as Equations or expression 1–11 above may be constructed and a similar process as that described above in reference to FIG. 6 may be conducted to derive the ellipsometric and system parameters. In the case where elements 106, 112 are phase modulators, each of these elements has a fast and a slow axis. One of the two axes is treated as the axis of the element, and the same analysis above may be applied for measuring and deriving the ellipsometric parameters n, k and the system parameters. The same is true if one or more of elements 106, 112 is a composite of one or more phase modulators and one or more polarizers.

The above described method is also applicable to system 10 of FIG. 1. Thus, the output of detector 28 is then used in the above analysis for deriving the ellipsometric and system parameters such as those enumerated above for elements 12, 14, 16, 18, 22, 24 and 26.

From the analysis set forth above, 25 harmonics are adequate for solving or deriving the ellipsometric or system parameters. In some applications, not all 25 harmonics are required for deriving such parameters. In such event, systems simpler than those indicated in FIGS. 1 and 3 may be used instead. Such configurations are illustrated in FIGS. 7A–7H. To simplify the drawings, the light source, detector and data acquisition and analysis device have been omitted. FIGS. 7A–7B illustrate conventional ellipsometers employing two polarizers. In FIG. 7A, unpolarized light is passed through a rotating polarizer 206 and supplied to sample 20. The radiation reflected by the sample is passed through a fixed polarizer 226 and sent to a detector for deriving ellipsometric parameters. In FIG. 7B, unpolarized radiation is passed through a fixed linear polarizer 214 and applied to the sample 20. The reflected radiation is then passed through a rotating polarizer 212 before it is applied to the detector for derivation of the ellipsometric parameters.

The configurations illustrated in FIGS. 7C–7H are possible and may be advantageously used in accordance with this invention. Thus, in FIG. 7C, unpolarized radiation is passed through a rotating polarizer 206 and applied to the sample 20 and the radiation modified by the sample is then passed through a rotating analyzer 212 and sent to a detector such as detector 28 or spectrometer 120, depending on whether the radiation is single wavelength or broadband. In FIG. 7D, unpolarized radiation is first passed through a fixed polarized 214 and then through a rotating polarizer 206 and applied to the sample 20. The modified radiation is passed to a fixed analyzer 226 to a detector. In FIG. 7E, unpolarized radiation is passed through a fixed polarizer 214, modified by sample 20 and applied through a rotating analyzer 212 and then a fixed analyzer 226 to a detector. In FIG. 7F, unpolarized radiation is passed through a fixed polarizer 214, a rotating polarizer 206 to sample 20 and the radiation modified by the sample is passed to a rotating analyzer 212 to the detector. In FIG. 7G, unpolarized radiation is passed through a rotating polarizer 206 to the sample 20 and the radiation modified by the sample is passed through a rotating analyzer 212 and a fixed analyzer 226 to the detector. The configuration of FIG. 7H is similar to that of FIG. 3, except that no focusing mirrors are used.

Thus, in the configuration of FIGS. 7C, 7F, 7G and 7H, the radiation is modified by a rotating polarizer or analyzer before and after modification by the sample, where the radiation may also be passed through one or more or no fixed polarizing element. In the configurations of FIGS. 7D, 7E, the radiation is passed through a fixed polarizing element before and after modification by the sample but where only one rotating polarizer or analyzer is used to modify the radiation either before or after modification by the sample, but not both.

When the apparatuses or configurations of FIGS. 7C–7E are employed, five harmonics may be generated from the detected signal. Five harmonics may be adequate for deriving ellipsometric and system parameters for some applications. In certain applications, more harmonics may be necessary or desirable; for these applications, the configurations of FIGS. 7F, 7G, 7H and 3 would be desirable.

The above-described analysis may be modified slightly for any one of the above-described configurations in FIGS. 7C–7H. Obviously, where no mirrors are employed as in FIG. 3, system parameters involving these mirrors may be omitted in the analysis. Where no rotating polarizer is used to modify the radiation before the radiation is applied to the sample, the variable P representing the angle of the rotating axis of the rotating polarizer may be set to a constant or zero. Where no rotating analyzer is employed to modify the radiation after the radiation has been reflected or otherwise modified by the sample, the quantity A representing the angle of the rotating analyzer may also be set to a constant or zero. Aside from such differences, the above-described analysis may be applied to derive the ellipsometric parameters in the configuration of FIGS. 7C–7H.

While it is advantageous to derive system parameters together with ellipsometric parameters for the reasons discussed above, for some applications, it may be adequate to simply derive the ellipsometric parameters without also deriving the system parameters, such as in the configurations of FIGS. 3, 7C–7H. Such and other variations are within the scope of the invention.

In order to generate 25 harmonics, the two polarizers, modulators (18, 22 and 106, 112) should be rotated at different speeds. Where the speed of rotation of one polarizer or modulator is an integral multiple of the speed of rotation of the other in the pair, there may not be adequate information for all 25 harmonics to be derived from the detector signal. Therefore, in order to derive the 25 harmonics, it is desirable for the speed of rotation of each of the two polarizers or modulators to be an integer indivisible by the speed of rotation of the other polarizer or modulator. In other words, it is desirable for the largest lowest common denominator of the two integer speeds to be 1. Furthermore, in order to obtain adequate detector information, it is desirable for at least one of the two modulators or polarizers to be rotated by more than 13 complete revolutions while the detector signal is detecting radiation that has been modulated by the sample and by the modulator or polarizer.

The two polarizers or phase modulators may be rotated continually or intermittently. Where the rotation is intermittent, the detector may be used to detect while the phase modulators or the polarizers are stationary. Instead of using a rotating polarizer or a rotating retarder, a photoelastic modulator or Pockels cell may be used instead. The rotating retarder may be a Fresnel rhomb. The configurations of FIGS. 7A–7G may be arrived at by removing one or more of the elements 14, 106, 112, 26 from system 100 in FIG. 3; this may be accomplished by means of motors 250 in FIG. 3. The algorithm described above in reference to FIG. 6 and the equations may be performed by the data acquisition 30, which may simply be a computer.

FIG. 8A is a schematic diagram of a portion of the system in FIGS. 1 and of an apparatus for sensing sample tilt or height of the sample. As noted above, in conventional measurement systems, sample tilt or height is measured via an optical path which is different and separate from the measurement path. This renders the system cumbersome and sometimes inaccurate. The measurement of sample tilt and height is important since such inaccuracies may lead to errors in measurement despite a properly calibrated system. Thus, as shown in FIG. 8A, after being modified by the sample, the radiation is passed through a modulator such as the phase modulator 22 or rotating polarizer 112 and relayed by lens 24 through a fixed analyzer 26 to a grating 302. Most of the energy in the beam appears as the zeroth order ray which passes through an aperture 304 to detector 28. The radiation in the beam 13 is substantially monochromatic so that diffraction grating 302 would diffract the +1 order of the diffracted beam towards the detector 306. Detector 306 is placed so that the total optical path from lens 24 to grating 302 and from grating 302 to detector 306 is substantially equal to the focal length of lens 24. Therefore, even if surface 20a of sample 20 is instead at a lower level 20a', the +1 order ray from surface 20a' and grating 302 would still be directed in the same direction towards detector 306, so that the detection of detector 306 is not affect by change in sample height. Detector 306, however, would detect a tilt of the sample from position 20a to position 20a", which may cause the +1 order of the diffraction from grating 302 to change in direction. Therefore, if detector 306 has been calibrated where surface 20a is at the proper tilt, detector 306 may be used to detect sample tilt, where such detection is unaffected by change in sample height.

Detector 308 is positioned to detect the −1 order diffraction from grating 302. Detector 308 is calibrated to detect sample surface 20a at the proper height. Therefore, if surface 20a of the sample has been lowered (or raised) to position 20a' shown in dotted lines in FIG. 8A, this will cause a change in direction in the −1 diffraction and will be sensed by detector 308.

FIG. 8B is a schematic view of a portion of system 100 in FIG. 3 and of an apparatus for sensing sample tilt and change in sample height. Instead of using a grating which is wavelength dependent, two essentially transmissive but slightly reflective elements may be used instead, such as two pellicles shown in FIG. 8B. Thus, pellicles 312 and 314 may be placed in the optical path between fixed analyzer 26 and spectrometer 120. Both pellicles are placed in positions which are almost normal to the optical path, so that most of the radiation passes through the two pellicles but a small amount of radiation is reflected by the pellicles in directions slightly away from the optical path towards detectors 316 and 318, respectively. Detector 316 is positioned so that the total optical path length between mirror 110 and pellicle 312 and between pellicle 312 and detector 316 is substantially equal to the focal length of mirror 110. For reasons similar to those explained above in regard to detector 306 of FIG. 8A, it is possible to use detector 316 to detect sample tilt without being affected by change in sample height. Also similar to detector 308 of FIG. 8A, detector 318 has been calibrated to detect the sample surface 20a at a proper height, so that a change in sample height would be detected by detector 318.

Semiconductor manufacturing frequently reserves on a wafer a small electrical contact pad area which may be used for ellipsometric measurements, where the area frequently have square shapes. The illumination beam in ellipsometry is typically directed at an oblique angle to the sample. Therefore, if the illumination beam has a circular cross-section, the resulting illuminated spot on the sample will be elliptical in shape. Since the size of the square pads reserved for ellipsometry on semiconductors may be small in size, it may be difficult to fit the elliptical spot within such pad.

By using or adding a cylindrical objective to focus the illumination beam onto the sample, this would have the effect of flattening the elliptical spot to better fit within the confines of the pads. Preferably, the cylindrical objective focuses the illumination beam to a spot which is substantially circular in shape. Thus, the lens 16 in FIG. 1 may be a cylindrical lens, or a cylindrical lens may be added to FIG. 1 to focus beam 11, so as to flatten the illuminated spot on a sample 20. Similarly, the mirror 108 in FIG. 3 may also be a cylindrical mirror, or a cylindrical mirror may be added, so as to flatten the illuminated spot on sample 20. Preferably, the focusing power of the lens 16 or mirror 108, or of the lens and mirror combinations, in the plane of incidence is such that the illuminated spot is circular in shape.

The following description in reference to FIGS. 9–13B is essentially taken from parent application Ser. No. 09/246,922 filed on Feb. 9, 1999.

FIG. 9 is a schematic view of a combined instrument including a spectroscopic ellipsometer and a polarimetric system to illustrate the preferred embodiment of the invention of the parent application. Before the spectroscopic ellipsometer of the combined instrument is discussed, the polarimetric system 1008 is first described in some detail in reference to FIGS. 9 and 10. As indicated below, while preferably system 1008 is advantageously used together with a spectroscopic (or single wavelength) ellipsometer as in the combined instrument of FIG. 9, this system can also be advantageously used by itself for measuring samples.

The overall optical arrangement in polarimetric system 1008 resembles the spectroreflectometer described in U.S. Pat. No. 5,747,813 and retains its simplicity. However, different from such spectroreflectometer, system 1008 of the invention of the parent application measures polarimetric reflectance spectrum rather than polarization insensitive reflectance spectrum as in the system of U.S. Pat. No. 5,747,813. System 1008 is therefore more sensitive to surface properties than the system of U.S. Pat. No. 5,747,813. While in the preferred embodiment, the invention of the parent application is illustrated as detecting radiation reflected by the sample, it will be understood that the invention of the parent application will function essentially as described herein where radiation transmitted by the sample is detected instead; such and other variations are within the scope of the invention of the parent and this application. For simplicity, the preferred embodiment will be described below as measuring the reflected radiation, with the understanding that such description can be readily extended to measure the transmitted radiation.

The convention for showing the sample path, reference path, field illumination path, measurement illumination path and ellipsometer path are shown in the upper right-hand corner of FIG. 9. As noted above, the overall optical arrangement in the system for measuring polarimetric parameters is described below in reference to FIGS. 9 and 10.

Each of FIGS. 9 and 10 shows the same embodiment of an optical system according to the invention of the parent application for measuring polarimetric parameters. Part of the focusing and other optical elements of system 1008 and the spectroscopic ellipsometer of FIG. 9 are omitted in FIG. 10 to simplify the figure. The elements are explained below in conjunction with the figure which most clearly shows their placement with respect to other elements. Referring to FIG. 9, an optical system 1008 for measuring the relative reflectance spectrum of a wafer 1003 includes an illumination subsystem, a reflectometer subsystem, a viewing subsystem, and an autofocus subsystem, wherein any given optical element may be part of more than one subsystem. The illumination subsystem includes a lamp 1010, such as a xenon arc lamp, which emits a light beam 1012 of visible and/or ultraviolet (UV) light, a lamp housing window 1014, an off-axis paraboloidal mirror 1016, a flip-in UV cutoff filter 1018, a color filter wheel 1020, a flat mirror 1022, a concave mirror 1024, an aperture mirror 1028 with a flip-in 40 μm fine focus aperture 1030, a large achromat 1032, a field illumination shutter 1031, a fold mirror 1036, and a small achromat 1038. In FIG. 10, objective 1040 includes mirrors and a housing 1040' enclosing mirrors 1040a, 1040b, but leave sufficient spacing between the housing and the wafer for the oblique illumination beam from the spectroscopic ellipsometer (not shown in FIG. 10).

The illumination system provides a combined beam 1042 comprising a measurement beam 25 and a field illumination beam 1034. Lamp 1010 emits light beam 1012 through a lamp housing window 1014. The lamp housing window is not necessary for optical reasons; however it is provided to contain lamp 1010 should the lamp crack and explode. A xenon lamp is preferred over other lamps such as tungsten or deuterium lamps, because a xenon lamp will give a flatter output covering a spectrum from UV to near infrared. To provide a sample beam having components of wavelengths in a range including 190–220 nm, an additional deuterium lamp 1088 is used in combination with the xenon lamp 1010 to cover a broader spectrum that includes the deep UV. By using the two lamps together, the resulting combined spectrum of radiation supplied for detecting samples can be extended to a range of about 190 to 800 or 830 nm. Extending the spectrum to the deep UV range is useful for photolithography. Radiation from lamp 1088 is focused by lens 1093 and reflected by mirror 1095 to filter 1018 and combined with the radiation from the lamp 1010 to form the combined beam 1012'. By moving mirror 1095 into or out of the path of beam 1012 along arrow 1099, it is possible to include or exclude radiation from the deuterium lamp 1088 from the measurement beam 1025.

Off-axis paraboloid mirror 1016 collimates light beam 1012, which after combination with the radiation from the lamp 1088 to form beam 1012', can be optionally filtered by flip-in UV cutoff filter 1018 and color filter wheel 1020. Flip-in UV cutoff filter 1018 is used in part to limit the spectrum of light beam 1012', so that when light beam 1012' is dispersed by a diffraction grating, the first and second order diffraction beams do not overlap. Part of light beam 1012' is reflected by flat mirror 1022 onto concave mirror 1024 to form measurement beam 1025. Concave mirror 1024 focuses measurement beam 1025 onto the aperture in aperture mirror 1028.

Another part of light beam 1012, field illumination beam 1034, is focused by large achromat 1032 near fold mirror 1036, causing fold mirror 1036 to reflect an image of lamps 1010, 1088 toward small achromat 1038. Small achromat 1038 collects the light in field illumination beam 1034 before the light reflects off aperture mirror 1028. Aperture mirror 1028 is a fused silica plate with a reflective coating on one side, with a 150 μm square etched from the reflective coating to provide an aperture for measurement beam 1025. The aperture is placed at one conjugate of an objective 1040. The field illumination can be turned off by placing field illumination shutter 1031 in the optical path of field illumination beam 1034.

The narrow measurement beam 1025 and wide field illumination beam 1034 are rejoined at aperture mirror 1028, with field illumination beam 1034 reflecting off the front of aperture mirror 1028, measurement beam 1025 passing through the aperture and polarizer 1102, which may be moved into or out of the path of beam 1025 by a motor 1101.

FIG. 9 shows the reflectometer, viewing and autofocus subsystems of optical system 1008, including objective 1040, a beam divider mirror 1045, a sample beam 1046, an optional reference beam 1048, a concave mirror 1050, a flat mirror 1043, a reference plate 1052 with a reference spectrometer pinhole 1056, a sample plate 1054 with a sample spectrometer pinhole 1058, a second fold mirror 1068, a diffraction grating 1070, a sample linear photodiode array 1072, a reference linear photodiode array 1074, an achromat 1080 with a short focal length, mirror 1082, a beamsplitter cube 1084, a penta prism 1086, achromat 1090 with long focal lengths, a neutral density filter wheel 1097, a third fold mirror 1091, and a video camera 1096. Some of these components are not shown in FIG. 10, for clarity.

Several magnifications are possible for objective 1040. In one embodiment, a Schwarzchild design all-reflective objective may be mounted on a rotatable turret which allows for one of several different objectives (not shown) to be placed in the optical path of sample beam 1046. It is possible to include a refractive element of low power in the optical path of sample beam 1046 without significantly affecting the measurements in the invention of the parent application.

The measurement of the relative reflectance spectra of wafer 1003 will now be described. When field illumination shutter 1031 is placed in the path of field illumination beam 1034, combined beam 1042 comprises only measurement beam 1025. Combined beam 1042 is split by beam divider mirror 1045, a totally reflecting mirror placed so as to deflect half of combined beam 1042 towards objective 1040, thus forming sample beam 1046, the undeflected half of combined beam 1042 forming reference beam 1048. Because sample beam 1046 and optional reference beam 1048 are derived from the same source, lamps 1010 and 1088, and because combined beam 1042 is radially uniform, reference beam 1048 and sample beam 1046 have proportionally dependent spectral intensities. Furthermore, since beam divider mirror 1045 is a totally reflecting mirror in half of an optical path rather than a partially reflecting mirror in the entire optical path, a continuous broadband spectrum is reflected with good brightness.

Reference beam 1048 does not initially interact with beam divider mirror 1045, but instead illuminates concave mirror 1050. Concave mirror 1050 is slightly off-axis, so that reference beam 1048 is reflected onto the reverse face of beam divider mirror 1045, where flat mirror 1043 re-reflects reference beam 1048 into alignment with reference spectrometer pinhole 1056. Flat mirror 1043 is provided to realign reference beam 1048 with sample beam 1046 so that both beams pass through their respective spectrometer pinholes substantially parallel. This allows for simpler alignment of the spectrometer element for both channels, since the reference beam enters the spectrometer parallel to the sample beam.

Since reference beam 1048 does not interact with the surface of beam divider mirror 1045 which reflects beam 1046, there is no loss in reference intensity as reference beam 1048 passed beam divider mirror 1045. While reference beam 1048 does interact with a mirror 1043 on the reverse side of beam divider mirror 1045, these two mirrors are independent, since no light passed through beam divider mirror 1045. Indeed, in an alternative embodiment where the two reflecting surfaces of beam divider mirror 1045 cannot easily be placed together on one optical element, the reflecting surfaces exist on separate mirror elements.

The focal length of concave mirror 1050 is such that reference beam 1048 is in focus at reference spectrometer pinhole 1056. The light passing through reference spectrometer pinhole 1056 and reflecting off fold mirror 1068 is dispersed by diffraction grating 1070. The resulting first order diffraction beam is collected by reference linear photodiode array 1074, thereby measuring a relative reference spectrum.

Polarized sample beam 1046 is reflected off beam divider mirror 1045 towards objective 1040, where sample beam 1046 is focused onto wafer 1003, and the reflected sample beam 1046' is focused by objective 1040 onto sample spectrometer pinhole 1058. The reflected sample beam 1046' does not interact with beam divider mirror 1045 on the reflected path, because reflected sample beam 1046' passed through the space behind beam divider mirror 1045, where reference beam 1048 also passes. The radiation from reflected sample beam 1046' from the sample 1003 passes through an analyzer 1104 before it reaches pinhole 1058. The light passing through sample spectrometer pinhole 1058 and reflecting off fold mirror 1068 is dispersed by diffraction grating 1070 according to wavelength of the light. As with the reference beam, the resulting first order diffraction beam of the sample beam is collected by sample linear photodiode array 1072, thereby measuring the sample polarimetric spectrum. Because the two beams cross at diffraction grating 1070, the photodiode array apparently aligned with sample beam 1046 in FIG. 10 is in fact the photodiode array for reference beam 1048, and vice versa. The polarizer 1102 and analyzer 1104 do not rotate and are preferably stationary. Analyzer 1104 therefore analyzes the radiation modified by the sample and collected by objective 1040 according to a fixed plane of polarization.

The relative reflectance spectrum can then be simply obtained by dividing the sample light intensity at each wavelength by the relative reference intensity at each wavelength. Typically, this might involve 512 division computations, where 512-diode linear photodiode arrays are used to record the sample and reference spectra. In the preferred embodiment, the spectrum ranges from about 190 nm to 800 or 830 nm.

In one embodiment of the present invention of the parent application, diffraction grating 1070 is a concave holographic grating and the spectrometer pinholes are 15 mm apart. The diffraction grating is holographically corrected to image multiple spectra, since the 15 mm spacing does not allow for both beams to be centered on the grating. One such grating is a multiple spectra imaging grating supplied by Instruments S.A. Also, the grating is designed so that the angle of the detector causes reflections off the detector to fall away from the grating.

Combined beam 1042, which may include field illumination, is reflected off beam divider mirror 1045 toward wafer 1003. When reflectance spectra measurements and autofocusing are being performed, the field illumination is off to minimize scattered light.

The polarimetric system 1008 in FIGS. 9 and 10 differs from that described in U.S. Pat. No. 5,747,813 in that the sample beam 1046 is polarized in the system of this application. Thus, when the sample beam 1046 is reflected by objective 1040 towards the sample 1003, the beam that is focused onto the wafer has a multitude or a plurality of different polarization states. This is illustrated more clearly in reference to FIGS. 11A, 11B. Sample beam 1046 is reflected by mirror 1040a towards mirror 1040b which then focuses the beam towards the sample 1003 as shown in FIG. 11A. FIG. 11B is a schematic view of the illumination aperture of the sample beam 1046 when focused onto the wafer 1003. The various quantities in FIGS. 11A, 11B are defined by reference to cylindrical coordinates $\rho$, $\phi$ and $\theta$, where $\rho$ is the radius of a point (distance to the origin) in the coordinate system, $\phi$ the angle of a plane normal to the sample surface containing the point to a reference plane normal to the surface of the sample, and θ the angle from the normal to the sample surface of a line connecting the point to the origin (angle of incidence to the normal).

In reference to FIG. 11A, it is assumed that polarizer 1102 has a plane of polarization defined by the plane at $\phi_p$, so that the sample beam 1046 that emerges from the polarizer and reflected by beam divider 1045 also has this polarization. When beam 1046 is reflected first by mirror 1040a and then by mirror 1040b which focuses the beam onto the sample 1003, the beam that is focused onto the sample 1003 arrives in different planes of incidence as illustrated in FIGS. 11A, 11B. In FIG. 11B, the plane of polarization $\phi_p$ of the beam 1046 is indicated at 1103.

From the description above, beam divider mirror 1045 deflects about half of the polarized beam to become the sample beam 1046 and passes the remaining half of the beam as the reference beam 1048. For this reason, the illumination aperture (shaded area 1106) in FIG. 11B appears to be approximately semicircular in shape. Thus the radiation that is focused onto sample 1003 by objective 1040 will be incident onto the sample at planes of incident that span the semicircular area. The radiation incident on the wafer in one plane of incidence at one value of the angle ϕ in the area will have s- and p-polarizations that are different from those of radiation in a different plane of incidence having a different value of the angle ϕ in the area. The s- and p-polarizations of radiation in different planes of incidence will, by definition, have different orientations, so that the polarization state of the incident radiation in one plane of incidence will be different from that of the incident radiation in a different plane of incidence. Therefore, the radiation incident upon sample 1003 will have a multitude or plurality of polarization states as a function of ϕ.

The beam that is focused onto sample 1003 will be reduced in intensity compared to sample beam 1046 as a function of the combined reflection coefficients of the objectives 1040a, 1040b as explained below. The radiation originating from sample beam 1046 and focused onto the sample by objective 1040 is reflected by the sample which again reduces the intensity and changes the phase of each polarization component as a function of the reflection coefficients of the sample. Such radiation is again reflected by objective 1040 through beam divider 1045 and analyzer 1104 to the spectrometer as described above. While in the preferred embodiment, the same objective used for focusing the radiation onto the sample is also used for collecting the reflected radiation towards the analyzer and spectrometer; it will be understood that this is not required, and a different collection objective may be used in addition to the focusing objective; such and other variations are within the scope of the invention of the parent and this application.

Consider the radiation incident from point 1105 with coordinates (ρ, ϕ) of FIG. 11B in the semicircular illumination aperture with the polarization along the $\phi_p$ direction towards the origin on the sample surface. The electric field at this point can be decomposed in the s- and p-polarizations shown in FIGS. 11A, 11B as follows:

$$\vec{E}_{in} = E_0 \hat{p}_p = E_s^{in} \hat{\phi} + E_p^{in}(-\hat{\rho})$$

$$E_s^{in} = E_s^{in} \hat{p}_p \cdot \hat{\phi} = E_0 \sin(\phi_p - \phi)$$

$$E_p^{in} = E_0 \hat{p}_p \cdot (-\hat{\rho}) = -E_0 \cos(\phi_p - \phi) \quad (12)$$

where $E_{in}$ is the electric field of the radiation in beam 1046 after being polarized by the polarizer 1102, $E_0$ its amplitude, and $E_s^{in}$, $E_p^{in}$ the components of the radiation along the s- and p-polarizations. After the radiation exits the objective, $$\vec{E}_{out} = E_s^{out} \hat{\phi} + E_p^{out}(-\hat{\rho})$$

$$E_s^{out} = E_0 r_s^o r_s^s \sin(\phi_p - \phi)$$

$$E_p^{out} = -E_0 r_p^o r_p^s \cos(\phi_p - \phi) \quad (13)$$

where $E_{out}$ is the electric field of the radiation in beam 1046 after being reflected by the sample 1003, and $E_s^{out}$, $E_p^{out}$ its components along the s- and p-polarizations; and where $r_s^s(r_s^o)$ and $r_p^s(r_p^s)$ are the reflection coefficients for the s- and p-polarizations for the sample (objective). The reflection coefficients for the objective are the product of the reflection coefficients of the two mirrors as shown in FIG. 11A, i.e., $r_s^o = r_s^{o1} r_s^{o2}$ and $r_p^o = r_p^{o1} r_p^{o2}$. The electric field at the spectrometer after passing through the analyzer with polarization plane at $\phi_a$ will be along $\hat{p}_a$ can be obtained:

$$\vec{E}_{spectrometer} = \quad (14)$$

$$E_0 r_s^o r_s^s \sin(\phi_p - \phi) \sin(\phi_a - \phi) \left[ 1 + \frac{r_p^o r_p^s}{r_s^o r_s^s} \cot(\phi_p - \phi) \cot(\phi_a - \phi) \right] \hat{p}_a$$

The detector current can be expressed as $$I_{det} \propto \int_0^{\phi_o} \int_0^{\rho_o} \rho \, d\rho \, d\phi |E_{spectrometer}|^2 \quad (15)$$

If the polarizer 1102 is omitted, then the detector current for semicircular apertures becomes $$I_{det} \propto \frac{1}{2} |E_0|^2 [R_s^o R_s^s + R_p^o R_p^s] \quad (16)$$

In equation (16), $R_s^o$, $R_s^s$, $R_p^o$, $R_p^s$ are defined respectively as $|r_s^o|^2$, $|r_s^s|^2$, $|r_p^o|^2$, $|r_p^s|^2$. One must keep in mind that $r_s^o$, $r_s^s$, $r_p^o$, and $r_p^s$ are functions of the angle of incidence, i.e., functions of ρ. Where polarizer 1102 is in place as shown in FIGS. 9–11B, a general equation can be derived where the intensity at the spectrometer is a function of the s- and p-reflectivities of the sample and of the objectives and of $\Delta^o$, $\Delta^s$ which are defined by the equations $r_p^o/r_s^o = \tan \psi^o e^{j\Delta^o}$, $r_p^s/r_s^s = \tan \psi^s e^{j\Delta^s}$, (where $r_p^s$, $r_s^s$ are the complex reflection coefficients of the sample surface of radiation at p- and s-polarizations and where $r_p^o$, $r_s^o$ are the complex reflection coefficients of the objectives of radiation at p- and s-polarizations), where $\psi^o$, $\psi^s$, $\Delta^o$ and $\Delta^s$ are also the ellipsometric parameters. Therefore, system 1008 is polarization sensitive.

Shown below are some special cases:

A. $\phi_0 = \pi$ (17)

$$I_{det} \propto \int_0^{\rho_o} \rho \, d\rho |E_0|^2 \left[ R_s^o R_s^s \left( \frac{\pi}{4} + \frac{\pi}{8} \cos(2\phi_p - 2\phi_o) \right) + \right.$$

$$R_p^o R_p^s \left( \frac{\pi}{4} + \frac{\pi}{8} \cos(2\phi_p - 2\phi_o) \right) +$$

$$\left. \frac{\pi}{4} \cos(2\phi_p - 2\phi_o) \sqrt{R_s^o R_s^s R_p^o R_p^s} \cos(\Delta^o + \Delta^s) \right]$$

For the system to be sensitive to the change in $\Delta$, $2(\phi_p-\phi_a)=$ m$\pi$. If $\phi_p=\phi_a$, $$I_{det} \propto \frac{\pi}{8}\int_0^{\rho_o} \rho d\rho |E_0|^2 \left[3R_s^oR_s^s + 3R_p^oR_p^s + 2\sqrt{R_s^oR_s^sR_p^oR_p^s}\cos(\Delta^o+\Delta^s)\right] \quad (18)$$

B. $\phi_0=\pi/2$ (19)

$$I_{det} \propto$$

$$\frac{\pi}{8}\int_0^{\rho_o} \rho d\rho |E_0|^2 \left[R_s^oR_s^s\left(\frac{\pi}{4}+\frac{\pi}{8}\cos(2\phi_p-2\phi_o)-\frac{1}{4}\sin(2\phi_p)-\frac{1}{4}\sin(2\phi_p)\right)+\right.$$

$$R_p^oR_p^s\left(\frac{\pi}{4}+\frac{\pi}{8}\cos(2\phi_p-2\phi_o)+\frac{1}{4}\sin(2\phi_p)+\frac{1}{4}\sin(2\phi_p)\right)+$$

$$\left.\frac{\pi}{8}\cos(2\phi_p-2\phi_o)\sqrt{R_s^oR_s^sR_p^oR_p^s}\cos(\Delta^o+\Delta^s)\right]$$

If $\phi_p=\phi_a=\pi/2$, (20)

$$I_{det} \propto \frac{\pi}{8}\int_0^{\rho_o}\rho d\rho|E_0|^2 \left[R_s^oR_s^s\left(\frac{3\pi}{8}-\frac{1}{2}\right)+\right.$$

$$\left.R_p^oR_p^s\left(\frac{3\pi}{8}+\frac{1}{2}\right)+\frac{\pi}{8}\sqrt{R_s^oR_s^sR_p^oR_p^s}\cos(\Delta^o+\Delta^s)\right]$$

From the above analysis, the $\cos(\Delta^o+\Delta^s)$ coefficients in the third term in equations (18) and (20) are the largest when the polarizer and analyzer angles are the same, that is, when the polarizer 1102 and the analyzer 1104 have substantially the same plane of polarization. In other words, we can use a single polarizer to act both as the polarizer and analyzer as shown in FIG. 12. As shown in FIG. 12, the polarizer 1116 may be used to replace the polarizer 1102 and analyzer 1104. The sample channel of the photodiode array will be proportional to equation (19). In this configuration, only one polarizer is needed, and the polarizer and analyzer are self-aligned. As yet another alternative, the polarizer 1102 and analyzer 1104 may be omitted altogether if the divider 1045 is a polarizing beam splitter. For improved sensitivity of film thickness detection, a waveplate or other retarder element 1190 shown in dotted line may be inserted between the beam divider 1045 and analyzer 1104 in FIG. 9, to introduce a phase shift in the argument of cosine coefficients $\cos(\Delta^o+\Delta^s)$ in the third term in equations (18) and (20). Preferably, the phase shift in the collected radiation caused by the element 190 prior to analyzing and dispersion is about $\pi/4$. The thickness of the mirror coating of the mirrors 1040a, 1040b may also be selected to enhance sensitivity in detection of thicknesses of thin films so that the total change in phase in the radiation focused and collected by the mirrors 1040a, 1040b is about $\pi/2$. This will then cause $\Delta^o$ to be $\pi/2$ in the argument of cosine coefficients $\cos(\Delta^o+\Delta^s)$ in the third term in equations (18) and (20), so that the cosine term in these equations converts to a sine term.

The polarimetric spectrum measured in terms of the detector currents in array 1072 may be used for deriving useful information about the sample 1003. For example, if the types of materials in a number of different layers on sample 1003 are known so that one can estimate their refractive indices, such detector currents may be adequate for deriving the thicknesses and accurate refractive indices of the layers. Methods for such derivation is known to those skilled in the art and need not be discussed in detail here. Alternatively, the detector signals may be combined with ellipsometry measurements for deriving film thicknesses and refractive indices. Using broadband radiation for detection in the polarimetric system is advantageous, since one can obtain data points at a number of different wavelengths. Such wealth of data points is very useful for determining the thicknesses and refractive indices of multiple layers on the sample, and may permit one to apply more accurate curve fitting algorithms or to cross-check the accuracy of the measurements.

System 1008 can also be used for detecting other parameters of the sample surface. From the equations and the description above in reference to the Figures, especially FIGS. 11A and 11B, the reflected spectrum detected by spectrometer of photodiode array 1072 use information concerning $\Delta$, a polarimetric parameter commonly used in ellipsometry and related to thicknesses and refractive indices of thin films at the surface of the sample. Therefore, if certain aspects of the sample surface are known, such known aspects may be combined with the information concerning polarimetric parameters measured by system 1008 to derive useful information on the sample, such as film thicknesses and refractive indices.

In the preferred embodiments, the reflected spectrum obtained from photodiode array 1072 is compared to the reference spectrum from photodiode array 1074 to derive polarimetric parameters, thereby improving signal to noise ratio. For some applications, however, such polarimetric parameters may be derived from the reflected spectrum alone, without the use of a reference spectrum. For such applications, the reference beam 1048 is not required, so that all the components associated with the generation of beam 1048 and the reference spectrum may be omitted in FIGS. 9 and 10. Such and other variations are within the scope of the invention of the parent and this application.

The spectroscopic ellipsometer 1300 in the combined instrument of FIG. 9 will now be described. As shown in FIG. 9, a portion of the radiation originating from the xenon arc lamp 1010 that has passed through focus 1018 and 1020 is diverted by a beam splitter 1302 to a fiber optic cable 1304 which supplies the radiation to a collimator 1306. After being collimated, the beam is polarized by polarizer 1310 and is focused by focus mirror 1312 to the wafer 1003. The reflection of such beam is collected by a collection mirror 1314 and reflected by folding mirror 1316 through an analyzer 1320 before it is supplied to spectrometer 1322 and detector 1324 for detection. The polarizer 1310 and analyzer 1320 are rotated relative to each other so that the amplitude and phase of the change in polarization state of the beam 1308 caused by the reflection at the wafer 1003 can be measured. For a more detailed description of the operation of the spectroscopic ellipsometer 1300, please see U.S. Pat. No. 5,608,526.

To measure a sample with layers of thin film, it may be desirable to employ a combined instrument, including system 1008 for measuring polarimetric parameters and spectroscopic ellipsometer 1300, as shown in FIG. 9. System 1008 and spectroscopic ellipsometer 1300 are arranged so that sample beam 1046 and sample beam 1308 are focused onto substantially the same spot on the wafer 1003. The polarimetric parameters measured by system 1008 may then be combined with the ellipsometric parameters measured by system 1300 for deriving useful information such as film thicknesses and film refractive indices. The polarimetric parameters obtained by system 1008 and the ellipsometric parameters obtained using system 1300 may be combined using techniques such as that described in "ANALYSIS OF SEMICONDUCTOR SURFACES WITH VERY THIN NATIVE OXIDE LAYERS BY COMBINED IMMERSION AND MULTIPLE ANGLE OF INCIDENCE ELLIPSOMETRY", Ivan OHLIDAL and Frantisek LUKES, Applied Surface Science 35 (1988–89) 259–273, North Holland, Amsterdam.

Even though the spectral range of some spectroscopic ellipsometers does not extend to the deep UV such as about 157 nm, by using the combined instrument, it is possible to accurately measure the indices of refraction at such wavelength. Thus, the combined instrument may be used for measuring the indices of refraction over the combined spectra of the spectroscopic ellipsometer and the polarimeter system 1008. By using the combined instrument, and data from both system 1008 and from the spectroscopic ellipsometer, the thicknesses and refractive indices of different films of the sample at wavelengths in the spectrum of the spectroscopic ellipsometer can be found. This thickness information may be used together with data from the combined instrument to find the refractive indices of the films in the deep ultraviolet region. The numbers of detectors in the arrays 1072, 1074 and detector 1324 in spectrometer 1322 may be chosen to obtain data at the desired wavelengths for optimum results.

In an alternative embodiment, sample beams 1046 and 1308 need not be focused on the same spot on wafer 1003. Wafer 1003 may be moved by rotation or linear translation, or a combination of the two motions, in a conventional manner so that spots measured by system 1008 are subsequently measured by system 1300, or vice versa, and so that data obtained by the two systems measuring the same spot may be combined in the same manner as that described above. Since the rotational and translational of motions are controlled, the relative locations of the spots being measured by the two systems 1008 and 1300 can be correlated.

While preferably a spectroscopic ellipsometer is combined together with the polarimetric system 1008 as described, it is also possible to combine system 1008 with a single wavelength ellipsometer. For this purpose, the arrangement in FIG. 9 needs to be modified only slightly by removing the diffractive grating in the optical path of the spectrometer 1322, between mirror 1321 and detector 1324. A laser with wavelength in the polarimetric spectrum may be used as the radiation source for the single wavelength ellipsometer. With the measurements taken by means of the single wavelength ellipsometer and by means of system 1008, it is still possible to derive film thicknesses and indices of refraction at wavelengths over the polarimetric spectrum.

The above description in reference to FIGS. 9–13B is taken essentially from the parent application.

In order for ellipsometer 1300 of FIG. 9 to be self-calibrating, the ellipsometer needs to be modified in accordance with any one of the schemes in FIGS. 1, 3, and 7C–7H to provide five or more harmonics in order to provide adequate information to determine parameters of the ellipsometer as well as sample characteristics. In other words, the polarizer 1310 may be replaced by any one of the combinations involving one or both of rotating polarizer 206 and fixed polarizer 214 and the analyzer 1320 may be replaced by any one of the combinations of one or both of fixed analyzer 226 and rotating analyzer 212 shown in FIG. 7C–7H. Alternatively, ellipsometer 1300 may be modified by inserting a phase modulator (such as a phase retarder) in the path of radiation between the polarizer 1310 and the sample and/or the path between the sample and the analyzer 1320.

The output of spectrometer 1322 is processed by a processor (not shown but similar in function to processor 30) in the same manner as that described above for deriving various system parameters of the ellipsometer 1300 as well as ellipsometric parameters of the sample 1003, so that the ellipsometer 1300 becomes self-calibrating with all the attendant advantages described above. The self-calibrating characteristics of the ellipsometer 1300 may be advantageously applied to any other optical instrument used in conjunction with it, such as the polarimeter 1008 in FIG. 9. In one embodiment, both instruments 1008 and 1300 may be used for measuring the same sample 1003 and the outputs of both instruments may be used for deriving sample characteristics as well as the parameters of the ellipsometer 1300 to yield a more accurate measure of the sample 1003. In another embodiment, the self-calibrating ellipsometer 1300 may be used for calibrating the polarimeter 1008 as described below.

Ellipsometers are typically equipped with an internal reference sample kept in a relatively stable environment within the housing of the ellipsometer. In another embodiment, such internal reference sample of the ellipsometer, such as ellipsometer 1300, may be used to provide a standard for the calibration of other optical measurement instruments. Thus, if sample 1003 is the internal reference sample of ellipsometer 1300, the characteristics such as film thickness and indices of refraction of the sample may be accurately measured by the self-calibrating ellipsometer 1300 as described above, and such reference sample may then provide a calibration standard for other optical measurement instruments, such as the polarimeter 1008. Since the ellipsometer 1300 is self-calibrating, its calibration does not require any external calibration standards so that the user can be certain that the characteristics of the internal reference sample 1003 have been accurately measured in order to provide a calibration standard for other optical instruments.

Instead of combining a self-calibrating ellipsometer 1300 with the polarimeter 1008, the ellipsometer may be combined with a spectroreflectometer by simply removing the polarizer 1002 and analyzer 1004 from the polarimeter 1008. Obviously, where a narrow band radiation source is used instead of a broadband source, a narrow band reflectometer may be combined with the ellipsometer 1300. Alternatively, the self-calibrating ellipsometer 1300 may be used in combination with another ellipsometer (single wavelength or broadband) or any other type of optical sample measurement instrument. The outputs of both instruments may be used in essentially the same manner as described above to derive characteristics of the sample as well as parameters of the ellipsometer 1300, or of the other instrument combined with ellipsometer 1300. All such combinations are within the scope of the invention.

In International Application No. PCT/US98/11562, a stable wavelength calibration ellipsometer is used to precisely determine the thickness of a film on the reference sample. The measured results from the calibration ellipsometer are used to calibrate other optical instruments. However, in order for the stable wavelength calibration ellipsometer to provide a calibration standard, by precisely determining the thickness of the film on the reference sample, the stable wavelength calibration of the ellipsometer must itself be accurately calibrated. Thus, the calibration of the stable wavelength calibration ellipsometer may itself have to rely on other calibration standards which may or may not be readily available. The self-calibrating ellipsometer of this invention has no such drawbacks. Since the various parameters of the ellipsometer can be derived without any prior calibration or any reliance on other calibration standards, the above-described difficulties are avoided.

Certain sample characteristics such as surface roughness may cause depolarization of radiation applied to the sample. Thus, by measuring the depolarization of radiation caused by the sample, sample surface characteristics such as surface roughness may be ascertained. For an example of a depolarization measurement for determining surface roughness, please see "Rotating-compensator multichannel ellipsometry for characterization of the evolution of nonuniformities in diamond thin-film growth," Joungchel Lee et al., *Applied Physics Letters*, Vol. 72, No. 8, Feb. 23, 1998, pp. 900–902, which is incorporated herein in its entirety by reference. This may be performed by means of an ellipsometer (whether self-calibrating or not) to measure film thickness information and depolarization of radiation caused by the sample. Since the ellipsometer may be used to measure change in polarization state of the radiation caused by the sample, film thickness information as well as the depolarization caused by the sample may be determined from ellipsometric measurements, provided adequate information concerning such change in polarization state is obtained. This usually means that where the polarization state of the radiation is modulated at a frequency, and where the output of the ellipsometer provides signal components at five or more harmonics of such modulation frequency, adequate information is provided for determining the depolarization caused by the sample. Preferably, a self-calibrating ellipsometer of any one of the configurations in FIGS. 1, 3 and 7C–7H may be used to perform the measurement. Preferably, the ellipsometer 1300 is such that adequate information in the same measurement output is provided for deriving characteristics of the parameters of the ellipsometer as well as thickness information of and depolarizations caused by the sample; for some applications, the configuration of the ellipsometer is preferably such that the ellipsometer detector output contains signal components at more than five harmonics of the modulating frequency. It may also be preferable, in order to provide more information, for ellipsometer 1300 to measure over a spectrum of wavelengths to provide an output at different wavelengths over the spectrum. It is also possible to first perform a self-calibration procedure by means of the internal reference sample of the ellipsometer before the ellipsometer is then used to measure the film thickness information and depolarization of radiation caused by the sample.

The combined instrument 1300 and 1008 shown in FIG. 9 may be used to measure the depolarization of radiation caused by the sample, where in a single measurement, the outputs of both systems 1008 and 1300 are used to derive the film thickness information of the sample, depolarization of radiation caused by the sample as well as parameters of the ellipsometer 1300. This process is a simple extension of the technique described in the article by Ivan Ohlidal and Frantisek Lukes referenced above by including the various system parameters of the ellipsometer 1300 in the process. Such process is known to those skilled in the art in view of the present application and will not be described in detail herein. Preferably, the ellipsometer 1300 measures over a spectrum of wavelengths to provide adequate information for deriving sample characteristics and the system parameters of the ellipsometer.

While the invention has been described above by reference to various embodiments, it will be understood that changes and modifications may be made without departing from the scope of the invention, which is to be defined only by the appended claims and their equivalents. Thus, while a processor is used for performing the various calculations and algorithms described above, it will be understood that other circuits such as dedicated circuits, programmable logic and controllers for such calculations implemented in the form of discrete components or integrated circuits may be employed and are within the scope of the invention.

What is claimed is:

1. A method for measuring a sample, comprising:
   providing a beam of radiation;
   passing the beam through a first fixed or rotating polarizing element so that a polarized radiation from the beam is supplied to the sample;
   modulating radiation from the beam after modification by the sample by means of a second rotating linear polarizing element to provide a modulated beam;
   detecting radiation from the modulated beam;
   polarizing the modulated beam before radiation from the modulated beam is detected by means of a fixed linear polarizer; and
   deriving one or more ellipsometric parameters of the sample from the detected radiation.

2. The method of claim 1, further comprising rotating the first and second elements at different speeds.

3. The method of claim 2, wherein one of the two elements is rotated by more than 13 complete revolutions while the detecting detects radiation from the beam.

4. The method of claim 2, wherein the two elements are rotated at two speeds that form substantially a ratio of two integers, wherein each of the integers is indivisible by the other, while the detecting detects radiation from the beam.

5. The method of claim 1, wherein the two elements are rotated continually, or intermittently.

6. The method of claim 5, wherein the detecting detects said radiation during the continual rotation of the elements, or when the elements are substantially stationary when they are rotated intermittently.

7. The method of claim 1, wherein said providing includes passing unpolarized radiation through a fixed linear polarizer.

8. The method of claim 1, further comprising passing the modulated beam through a fixed linear polarizer before its detection.

9. The method of claim 1, wherein said providing provides a beam of broadband radiation.

10. The method of claim 1, wherein radiation in said beam has wavelengths spanning a range from about 190 to about 830 nm.

11. The method of claim 1, said deriving comprising deriving one or more parameters of the two elements, or of a system used in the providing, detecting or modulating.

12. The method of claim 11, wherein said deriving derives parameters of the system such that said ellipsometric parameters are accurately derived without prior calibration of the system or of the parameters of the two elements.

13. The method of claim 1, wherein said deriving derives one or more parameters that comprise an overall scale factor of the system, orientation of polarization axis or diattenuation of a polarizer, and polarization of any radiation in the beam.

14. A method for measuring a sample, comprising:
   providing a beam of polarized radiation having a linearly polarized component and supplying polarized radiation from the beam to the sample;
   detecting radiation from the beam that has been modified by the sample;
   modulating radiation from the beam before modification by the sample by means of a rotating linear polarizing element;

passing the modified radiation through a fixed or rotating linear polarizer prior to its detection; and deriving one or more ellipsometric parameters of the sample from the detected radiation.

15. The method of claim 14, wherein the element is rotated continually, or intermittently.

16. The method of claim 15, wherein the detecting detects said radiation during the continual rotation of the element, or when the element is substantially stationary when it is rotated intermittently.

17. The method of claim 14, wherein said providing includes passing unpolarized radiation through a fixed linear polarizer.

18. The method of claim 14, wherein said providing provides a beam of broadband radiation.

19. The method of claim 18, wherein radiation in said beam has wavelengths spanning a range from about 190 to about 830 nm.

20. The method of claim 14, said deriving including deriving one or more parameters of the two elements, or of a system used in the providing, detecting or modulating step.

21. The method of claim 20, wherein said deriving derives parameters of the system such that said ellipsometric parameters are accurately derived without prior calibration of the system or of the parameters of the two elements.

22. The method of claim 20, wherein said deriving derives one or more parameters that comprise an overall scale factor of the system, orientation of polarization axis or diattenuation of a polarizer, and polarization of any radiation in the beam.

23. An apparatus for measuring a sample, comprising:

a device providing a beam of radiation;

a first fixed or rotating polarizing element passing the beam so that a polarized radiation from the beam is supplied to the sample;

a second rotating linear polarizing element modulating radiation from the beam after modification by the sample to provide a modulated beam;

a fixed linear polarizer polarizing the modulated beam to provide a polarized modulated beam;

a detector detecting radiation from the polarized modulated beam; and means for deriving one or more ellipsometric parameters of the sample from the detected radiation.

24. The apparatus of claim 23, further comprising an instrument that causes the first and second elements to rotate at different speeds.

25. The apparatus of claim 24, wherein one of the two elements is rotated by more than 13 complete revolutions in response to the instrument while the detector detects radiation from the beam.

26. The apparatus of claim 24, wherein the two elements are caused to rotate at two speeds that form substantially a ratio of two integers, wherein each of the integers is indivisible by the other, while the detector is detecting radiation from the beam.

27. The apparatus of claim 23, wherein the two elements are caused to rotate continually, or intermittently.

28. The apparatus of claim 27, wherein the detector detects said radiation during the continual rotation of the elements, or when the elements are substantially stationary or when they are rotated intermittently.

29. The apparatus of claim 23, wherein said device comprises a source supplying unpolarized radiation and a fixed linear polarizer passing the unpolarized radiation.

30. The apparatus of claim 23, said device providing a beam of broadband radiation.

31. The apparatus of claim 23, wherein radiation in said beam has wavelengths spanning a range from about 190 to about 830 nm.

32. The apparatus of claim 23, said deriving means deriving one or more parameters of the two elements, or other elements of the apparatus.

33. The apparatus of claim 32, wherein said deriving means derives parameters of the apparatus such that said ellipsometric parameters are accurately derived without prior calibration of the system or of the parameters of the two elements.

34. The apparatus of claim 23, wherein said deriving means derives one or more parameters that comprise an overall scale factor of the apparatus, orientation of polarization axis or diattenuation of a polarizer, and polarization of any radiation in the beam.

35. A apparatus for measuring a sample, comprising:

a device providing a beam of polarized radiation having a linearly polarized component to the sample;

a rotating linear polarizing element modulating radiation from the beam and supplying the modulated beam to the sample which modifies the modulated beam;

a fixed or rotating linear polarizer polarizing radiation from the modulated beam after modification by the sample to provide a polarized modified beam;

a detector detecting radiation from the polarized modified beam; and means for deriving one or more ellipsometric parameters of the sample from the detected radiation.

36. The apparatus of claim 35, further comprising an instrument that causes the element to be rotated continually, or intermittently.

37. The apparatus of claim 36, wherein the detector detects said radiation during the continual rotation of the element, or when the element is substantially stationary, or when it is rotated intermittently.

38. The apparatus of claim 35, wherein said device comprises a source providing unpolarized radiation and a fixed linear polarizer passing the unpolarized radiation.

39. The apparatus of claim 35, wherein said device provides a beam of broadband radiation.

40. The apparatus of claim 39, wherein radiation in said beam has wavelengths spanning a range from about 190 to about 830 nm.

41. The apparatus of claim 35, said deriving means deriving one or more parameters of the element, the polarizer, or of other elements of the apparatus.

42. The apparatus of claim 35, wherein said deriving means derives parameters of the apparatus such that said ellipsometric parameters are accurately derived without prior calibration of the apparatus.

43. The apparatus of claim 35, wherein said deriving means derives one or more parameters that comprise an overall scale factor of the apparatus, orientation of polarization axis or diattenuation of a polarizer, and polarization of any radiation in the beam.

* * * * *